United States Patent
Chan et al.

(10) Patent No.: US 11,369,641 B2
(45) Date of Patent: Jun. 28, 2022

(54) IDENTIFICATION AND USES OF VASCULATURE FORMING PROGENITOR CELLS AND PROGENITOR CELL COMBINATIONS

(71) Applicant: The Board of Trustees of the Leland Stanford Junior University, Stanford, CA (US)

(72) Inventors: Charles K. F. Chan, Redwood City, CA (US); Andrew Stephen Lee, Palo Alto, CA (US); Michael T. Longaker, Atherton, CA (US); Irving L. Weissman, Stanford, CA (US); Joseph Wu, Stanford, CA (US); Divya Nag, Palo Alto, CA (US); Eun Young Seo, San Jose, CA (US)

(73) Assignee: The Board of Trustees of the Leland Stanford Junior University, Stanford, CA (US)

(*) Notice: Subject to any disclaimer, the term of this patent is extended or adjusted under 35 U.S.C. 154(b) by 514 days.

(21) Appl. No.: 16/323,079

(22) PCT Filed: Aug. 25, 2017

(86) PCT No.: PCT/US2017/048658
§ 371 (c)(1),
(2) Date: Feb. 4, 2019

(87) PCT Pub. No.: WO2018/039588
PCT Pub. Date: Mar. 1, 2018

(65) Prior Publication Data
US 2019/0183940 A1 Jun. 20, 2019

Related U.S. Application Data

(60) Provisional application No. 62/380,172, filed on Aug. 26, 2016.

(51) Int. Cl.
*A61K 35/35* (2015.01)
*A61K 35/28* (2015.01)
*C12N 5/0775* (2010.01)
*A61P 9/10* (2006.01)
*A61K 9/00* (2006.01)
*C12N 5/077* (2010.01)

(52) U.S. Cl.
CPC ............ *A61K 35/35* (2013.01); *A61K 9/0019* (2013.01); *A61K 35/28* (2013.01); *A61P 9/10* (2018.01); *C12N 5/0653* (2013.01); *C12N 5/0667* (2013.01)

(58) Field of Classification Search
None
See application file for complete search history.

(56) References Cited

U.S. PATENT DOCUMENTS

2010/0136114 A1 6/2010 Mao

FOREIGN PATENT DOCUMENTS

WO 2012/040408 A2 3/2012

OTHER PUBLICATIONS

Traktuev DO, Prater DN, Merfeld-Clauss S, Sanjeevaiah AR, Saadatzadeh MR, Murphy M, Johnstone BH, Ingram DA, March KL. Robust functional vascular network formation in vivo by cooperation of adipose progenitor and endothelial cells. Circ Res. Jun. 19, 2009;104(12):1410-20 (Year: 2009).*
Traktuev DO, Merfeld-Clauss S, Li J, Kolonin M, Arap W, Pasqualini R, Johnstone BH, March KL. A population of multipotent CD34-positive adipose stromal cells share pericyte and mesenchymal surface markers, reside in a periendothelial location, and stabilize endothelial networks. Circ Res. 2008 (Year: 2008).*
Bourin P, Bunnell BA, Casteilla L, Dominici M, Katz AJ, March KL, Redl H, Rubin JP, Yoshimura K, Gimble JM. Cytotherapy. Jun. 2013;15(6):641-8. (Year: 2013).*
Coby G. Suire, Nathalie Brouard, Brian Blaugrund, Paul J. Simmons. Isolation of the slromal/vascular fraction of murine bone marrow dramatically enhances MSC Yield, Allows isolation of Marrow endothelial cells and reveals multiple subpopulations of stromal cells Blood (2010) 116 (21): 3861 (Year: 2010).*
De Palma M, Venneri MA, Galli R, Sergi Sergi L, Politi LS, Sampaolesi M, Naldini L. Tie2 identifies a hematopoietic lineage of proangiogenic monocytes required for tumor vessel formation and a mesenchymal population of pericyte progenitors. Cancer Cell. Sep. 2005;8(3):211-26. (Year: 2005).*
Frazier TP, Bowles A, Lee S, Abbott R, Tucker HA, Kaplan D, Wang M, Strong A, Brown Q, He J, Bunnell BA, Gimble JM. Serially Transplanted Nonpericytic CD146(−) Adipose Stromal/Stem Cells in Silk Bioscaffolds Regenerate Adipose Tissue In Vivo. Stem Cells. Apr. 2016;34(4):1097-111. (Year: 2016).*
Rupnick MA, Panigrahy D, Zhang CY, et al. Adipose tissue mass can be regulated through the vasculature. Proc Natl Acad Sci U S A. 2002;99(16):10730-10735 (Year: 2002).*
Wagner W, Ho AD. Mesenchymal stem cell preparations—comparing apples and oranges. Stem Cell Rev. Dec. 2007;3(4):239-48. (Year: 2007).*
Badiavas AR, Badiavas EV. Potential benefits of allogeneic bone marrow mesenchymal stem cells for wound healing. Expert Opin Biol Ther. 2011;11(11):1447-1454. (Year: 2011).*

(Continued)

*Primary Examiner* — Peter Paras, Jr.
*Assistant Examiner* — Austin Jeffries
(74) *Attorney, Agent, or Firm* — Pamela J. Sherwood; Bozicevic, Field & Francis LLP

(57) ABSTRACT

Methods, compositions, and kits for producing functional blood vessels, and progenitors thereof are provided. Human disorders of the vascular system are treated by reconstitution of functional vessels in vivo through co-transplantation with supporting niche stromal cells for treatment of ischemic injury in the peripheral limbs and heart. The cell populations of the invention, when engrafted into a recipient, anastomose with host vasculature and regenerate functional blood vessels.

9 Claims, 10 Drawing Sheets

(56) References Cited

OTHER PUBLICATIONS

Champlin R. Selection of Autologous or Allogeneic Transplantation. In: Kufe DW, Pollock RE, Weichselbaum RR, et al., editors. Holland-Frei Cancer Medicine. 6th edition. Hamilton (ON): BC Decker; 2003. Available from: https://www.ncbi.nlm.nih.gov/books/NBK12844/ (Year: 2003).*

Maximiliano I. Schaun, Bruna Eibel, Melissa Kristocheck, Grasiele Sausen, Luana Machado, Andreia Koche, Melissa M. Markoski, "Cell Therapy in Ischemic Heart Disease: Interventions That Modulate Cardiac Regeneration", Stem Cells International, vol. 2016, Article ID 2171035, 16 pages, 2016. (Year: 2016).*

Kourosch et a."Human Mesenchymal Stromal Cells from Different Sources Diverge in Their Expression of Cell Surface Proteins and Display Distinct Differentiation Patterns", Stem Cells International, vol. 2016, Article ID 5646384, 9 pages, 2016. (Year: 2016).*

Thomas J. Kean, Paul Lin, Arnold I. Caplan, James E. Dennis, "MSCs: Delivery Routes and Engraftment, Cell-Targeting Strategies, and Immune Modulation", Stem Cells International, vol. 2013, Article ID 732742, 13 pages, 2013 (Year: 2013).*

Chi JT, Chang HY, Haraldsen G, et al. Endothelial cell diversity revealed by global expression profiling. Proc Natl Acad Sci U S A. 2003;100(19):10623-10628 (Year: 2003).*

Mora C, Tittensor DP, Adl S, Simpson AGB, Worm B (2011) How Many Species Are There on Earth and in the Ocean?. PLoS Biology 9(8): e1001127. (Year: 2011).*

Dinarello CA. Historical insights into cytokines. Eur J Immunol. 2007;37 Suppl 1(Suppl 1):S34-S45. (Year: 2007).*

Traktuev DO, Prater DN, Merfeld-Clauss S, Sanjeevaiah AR, Saadatzadeh MR, Murphy M, Johnstone BH, Ingram DA, March KL. Robust functional vascular network formation in vivo by cooperation of adipose progenitor and endothelial cells. Circ Res. Jun. 19, 2009;104(12):1410-20—Supplemental material (Year: 2009).*

Ankrum, J., Ong, J. & Karp, J. Mesenchymal stem cells: immune evasive, not immune privileged. Nat Biotechnol 32, 252-260 (2014). (Year: 2014).*

Li J, Ezzelarab MB, Cooper DK. Do mesenchymal stem cells function across species barriers? Relevance for xenotransplantation. Xenotransplantation. 2012;19(5):273-285. (Year: 2012).*

Macosko et al. Highly Parallel Genome-wide Expression Profiling of Individual Cells Using Nanoliter Droplets. Cell. May 21, 2015;161(5):1202-1214. (Year: 2015).*

Koh YJ, Koh BI, Kim H, Joo HJ, Jin HK, Jeon J, Choi C, Lee DH, Chung JH, Cho CH, Park WS, Ryu JK, Suh JK, Koh GY. Stromal vascular fraction from adipose tissue forms profound vascular network through the dynamic reassembly of blood endothelial cells. Arterioscler Thromb Vasc Biol. 2011;31(5):1141-50 (Year: 2011).*

Bianco et al., "The meaning, the sense and the significance: translating the science of mesenchymal stem cells into medicine", Nature Medicine, 2013, pp. 35-42, 19(1), Nature Publishing, London, United Kingdom.

Tang et al., "White Fat Progenitor Cells Reside in the Adipose Vasculature", Science, Oct. 24, 2008, pp. 583-586, vol. 322, Issue 5901, American Association for the Advancement of Science, Washington, D.C.

Chan et al., "Clonal precursor of bone, cartilage, and hematopoietic niche stromal cells", PNAS, Jun. 7, 2013, pp. 12643-12648, 110 (31), National Academy of Sciences, Washington, D.C.

Jain, "Molecular regulation of vessel maturalion", Nature Medicine, Jun. 2003, pp. 685-693, 9(6), Nature Publishing, London, United Kingdom.

Carmeliet et al., "Molecular mechanisms and clinical applications of angiogenesis", Nature, May 19, 2011, pp. 298-307, 473(7347), Nature Publishing, London, United Kingdom.

Huang et al., "Embryonic stem cell-derived endothelial cells engraft into the ischemic hindlimb and restore perfusion", May 2010, pp. 984-991, 30(5), American Heart Association, Inc., Dallas, TX.

Koh et al., "Stromal Vascular Fraction From Adipose Tissue Forms Profound Vascular Network Through the Dynamic Reassembly of Blood Endothelial Cells", Arteriosclerosis, Thrombosis, and Vascular biology, Mar. 10, 2011, pp. 1141-1150, 31(5), American Heart Association, Inc., Dallas, TX.

Kusuma et al., "Self-organized vascular networks from human pluripotent stem cells in a synthetic matrix", PNAS, Jul. 30, 2013, pp. 12601-12606, 110(31), National Academy of Sciences, Washington, D.C.

* cited by examiner

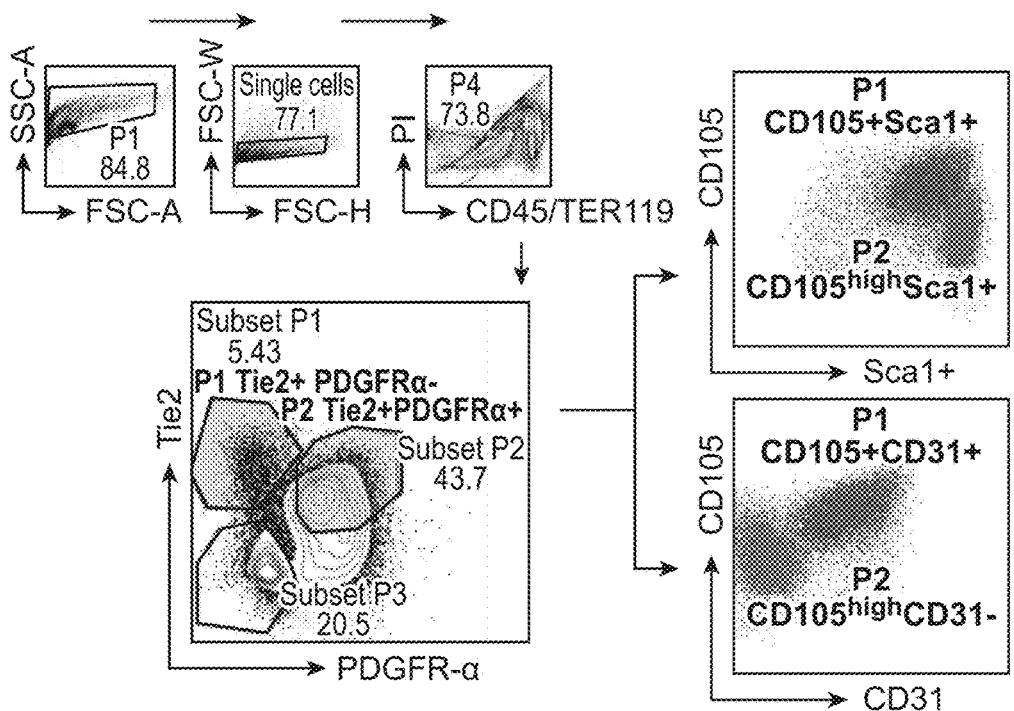
FIG. 1A
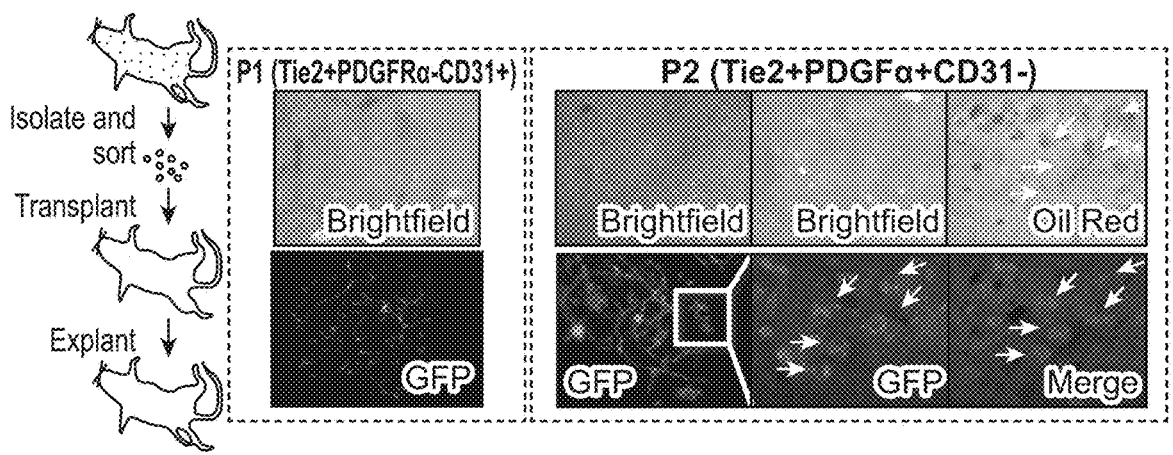
FIG. 1B  FIG. 1B(i)  FIG. 1B(ii)
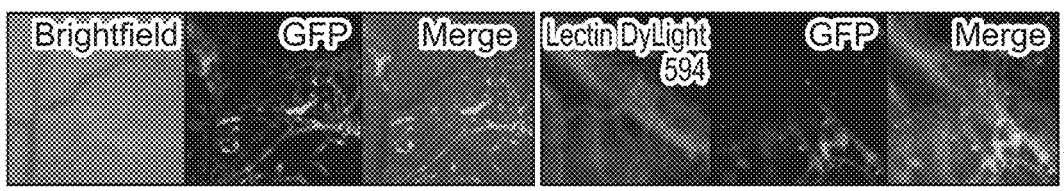
FIG. 1C  FIG. 1D
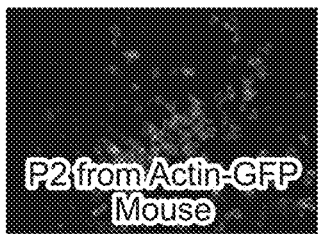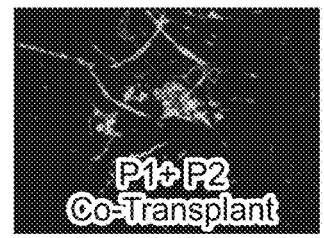
FIG. 1E

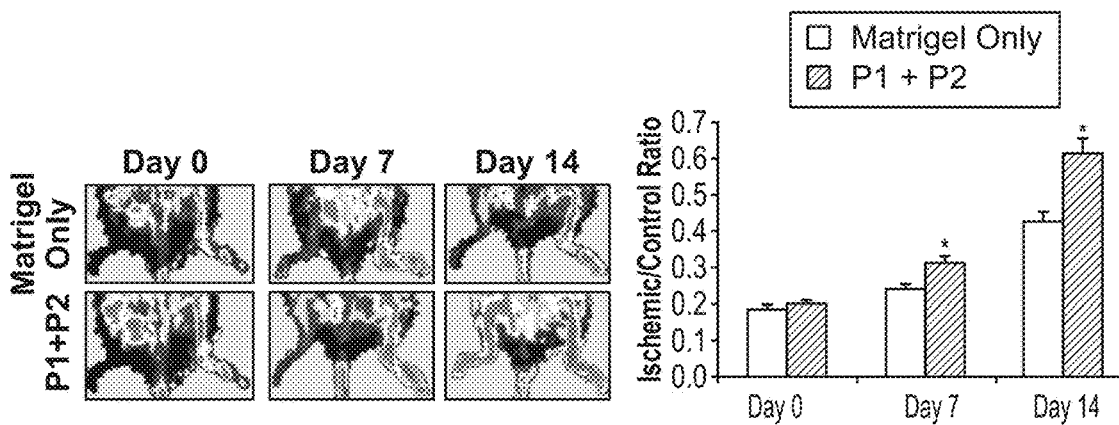

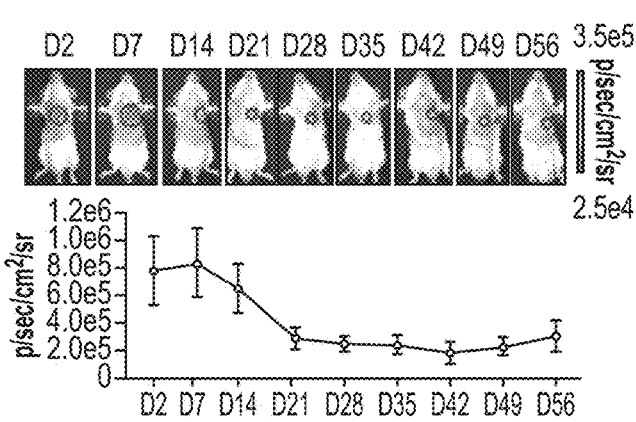
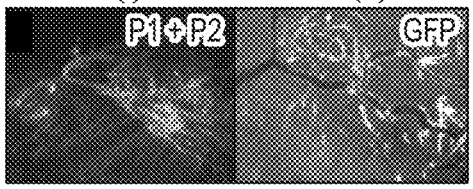

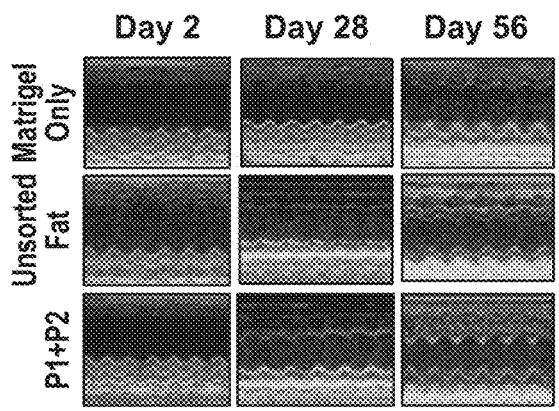
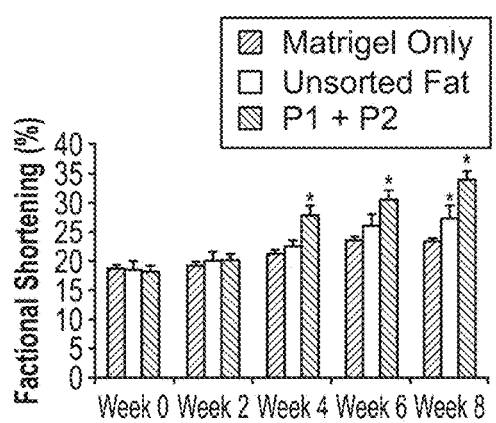
FIG. 2A  FIG. 2B  FIG. 2C(i)  FIG. 2C(ii)  FIG. 2C(iii)  FIG. 2C(iv)  FIG. 2D  FIG. 2E(i)  FIG. 2E(ii)  FIG. 2F(i)  FIG. 2F(ii)  FIG. 2F(iii)  FIG. 2G  FIG. 2H

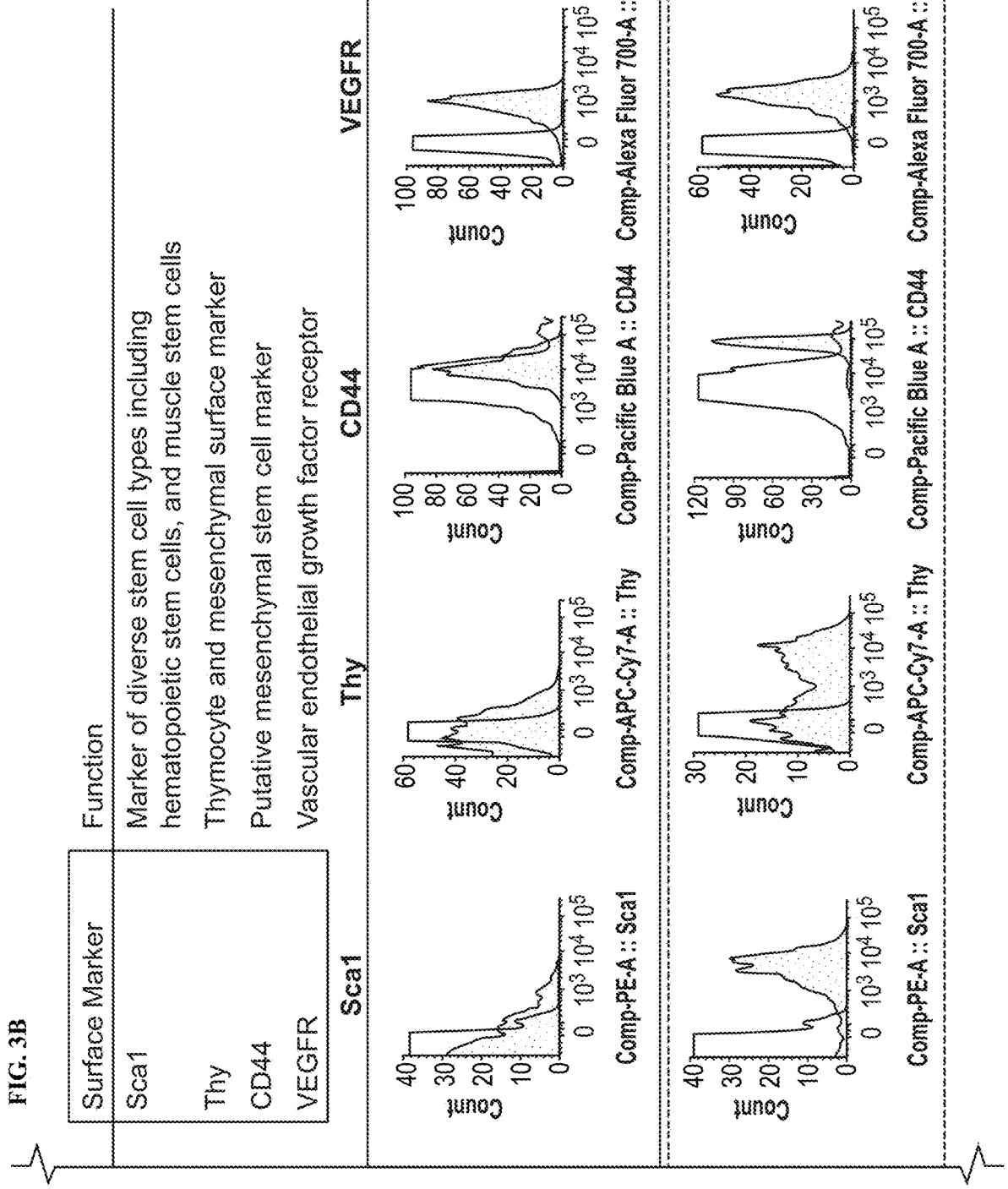

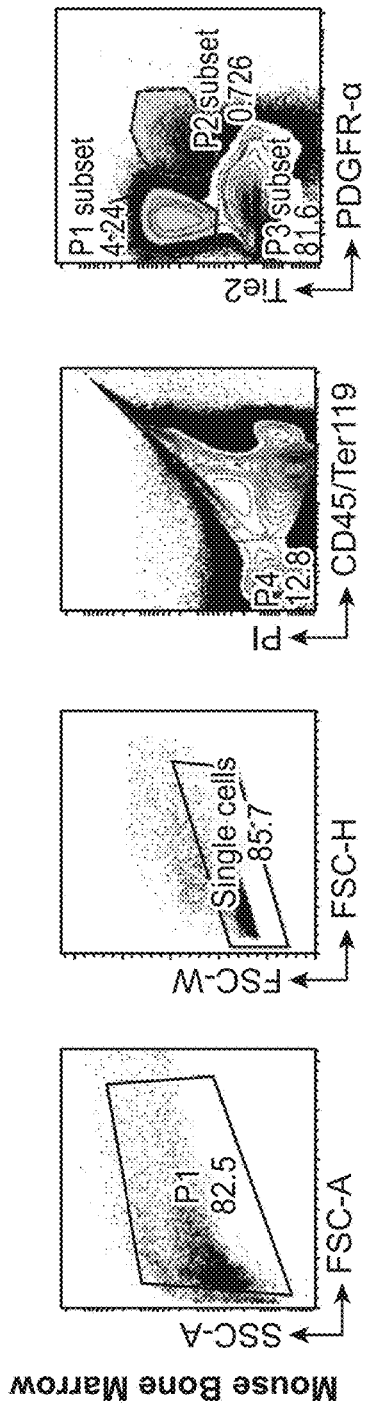
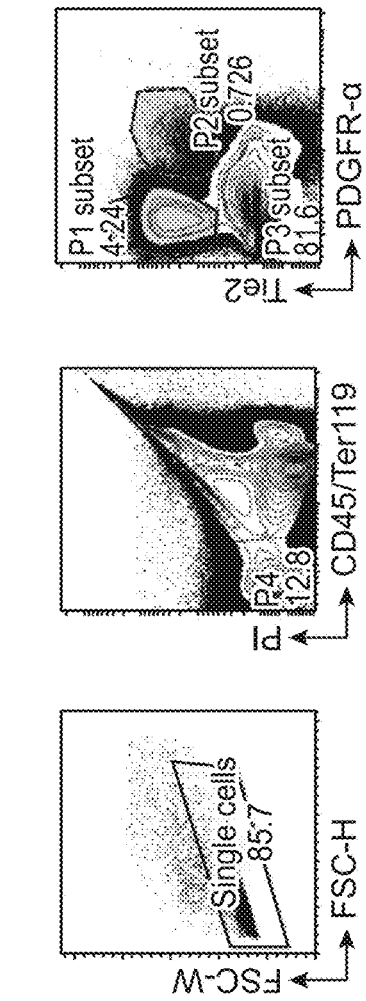
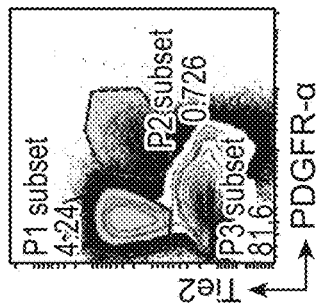
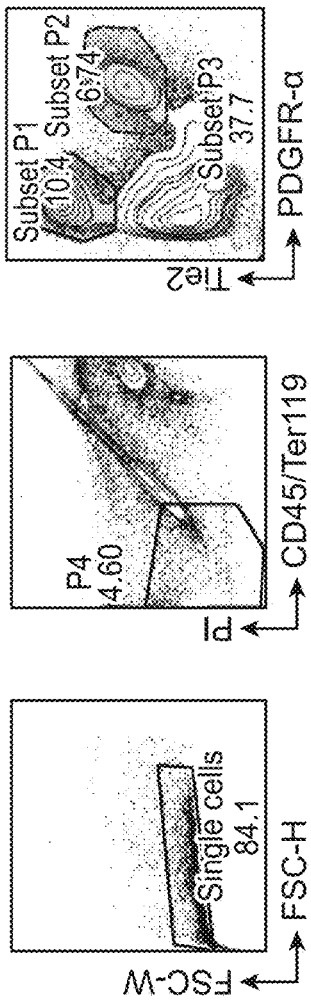
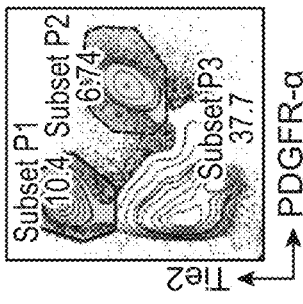
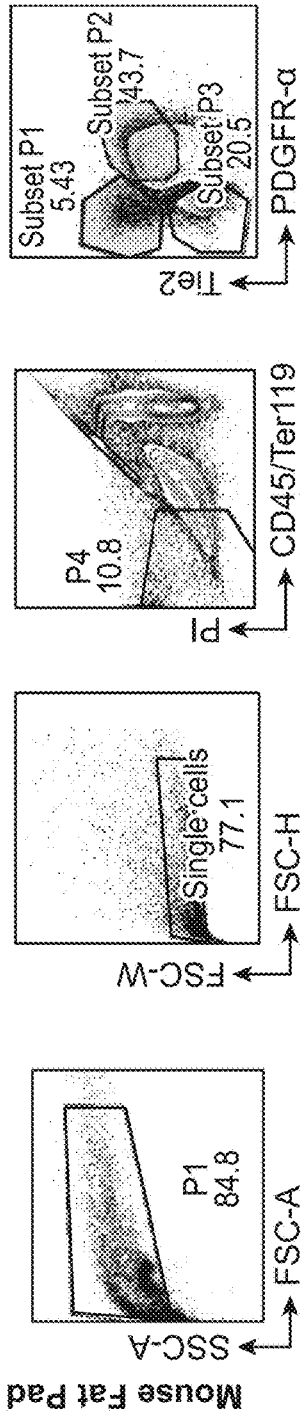
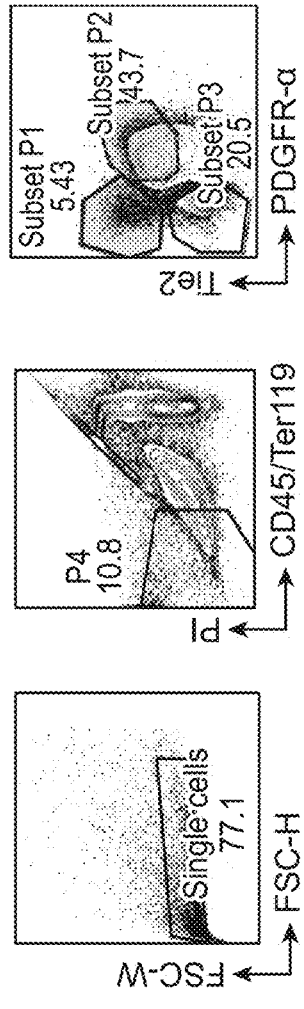
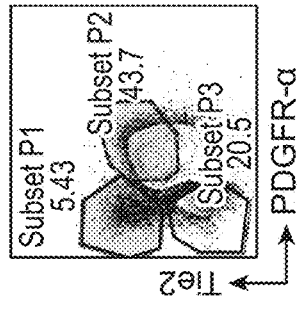
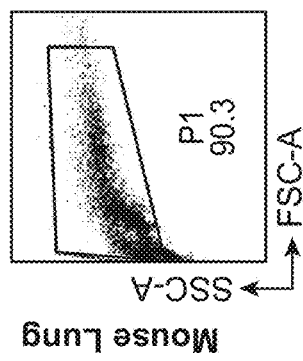
FIG. 4A, FIG. 4B, FIG. 4C FIG. 8C(ii)
FIG. 8C(iii)

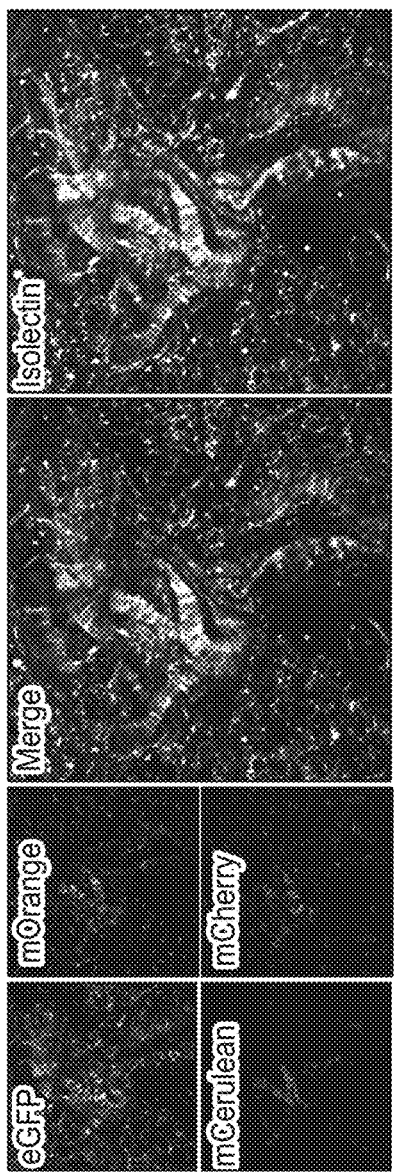
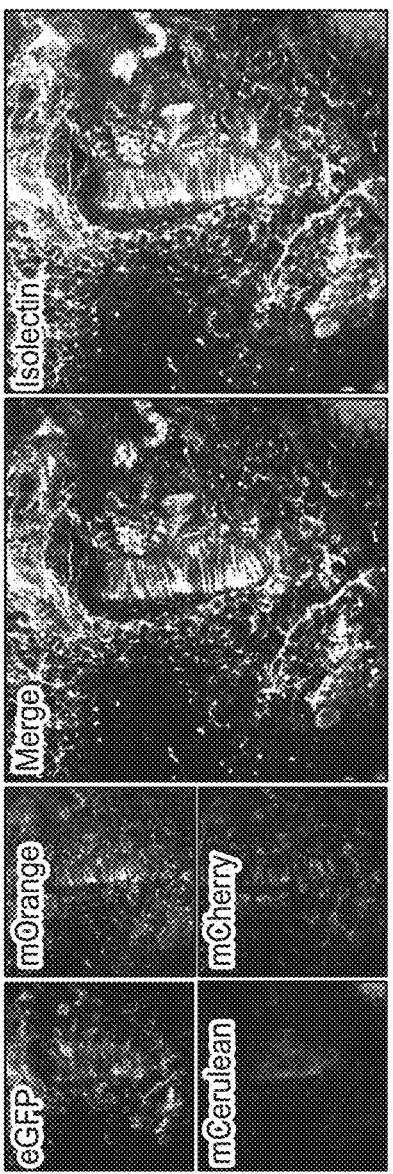
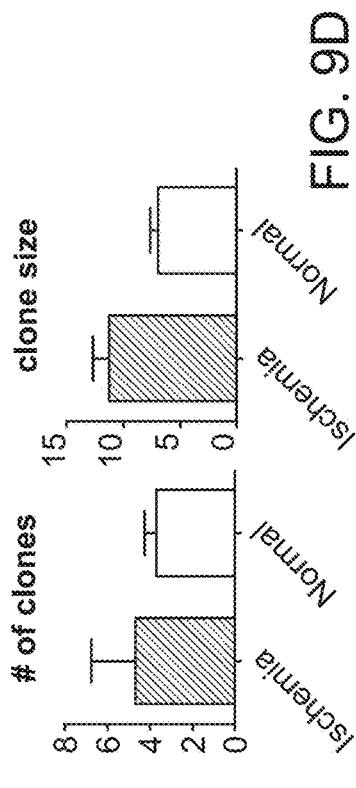
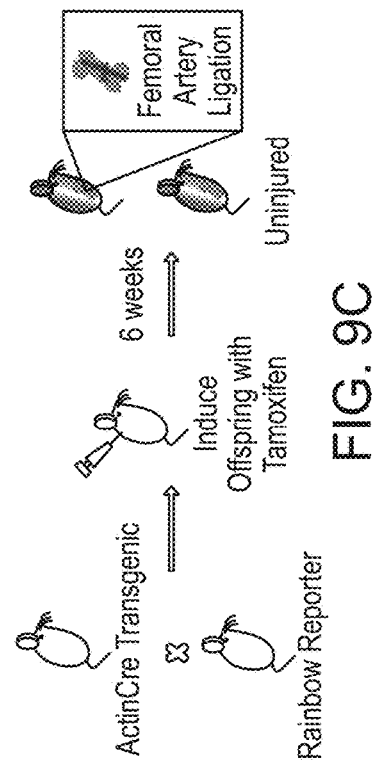
FIG. 9A
FIG. 9B
FIG. 9C
FIG. 9D

IDENTIFICATION AND USES OF VASCULATURE FORMING PROGENITOR CELLS AND PROGENITOR CELL COMBINATIONS

CROSS REFERENCE

This application claims benefit is a 371 application and claims the benefit of PCT Application No. PCT/US2017/048658, filed Aug. 25, 2017, which claims benefit of U.S. Provisional Patent Application No. 62/380,172, filed Aug. 26, 2016, which applications are incorporated herein by reference in their entirety.

FEDERALLY SPONSORED RESEARCH AND DEVELOPMENT

This invention was made with Government support under contracts DE020771, EB009689, HL058770, and HL089027 awarded by the National Institutes of Health. The Government has certain rights in the invention.

BACKGROUND OF THE INVENTION

Ischemic cardiovascular disease including coronary artery disease (CAD), peripheral arterial disease (PAD), and stroke is a leading cause of morbidity and mortality in the developed world and is estimated to affect over 20 million people in the United States alone. The identification of progenitor cell populations capable of treating vascular disease across the heart, brain, and peripheral limbs has thus been a central focus in stem cell biology translational medicine. In the past years, a number of studies have suggested the capacity of bone marrow and stromal subpopulations to form vascular cell lineages. However, to date none of these reports have been able to identify a distinct vessel progenitor population capable of giving rise to functional vasculature in vivo. Rather, the vast majority of studies employing these cell populations for treatment of ischemic injury attribute any therapeutic benefits observed to "paracrine effects" of transplanted cells rather than generation of functional vasculature by donor cell populations.

Mesenchymal stromal cells (MSCs) have been viewed as a potential source for vessel progenitors. Stromal progenitor cells are inherent to almost every organ of the human body that contains connective tissue. The term "mesenchymal stem cell" or "mesenchymal stromal cell" has traditionally been applied to encompass many of these progenitor cell classes including stromal cells derived from bone marrow, adipose tissue, and other organs. Recent studies have suggested, however, that contrary to early reports, MSCs are not a single multipotent population of cells that give rise to osteoid, adipose, endothelial, and myogenic progeny. Rather, these findings suggest MSCs are composed of distinct lineage-committed cell subsets, of which specific stromal cell populations give rise to distinct cell fates.

Identification of cells and factors capable of reconstituting functional vessels and vasculature in vivo is of great interest for both clinical and research applications. The present invention addresses this issue.

PUBLICATIONS

Bianco et al. The meaning, the sense and the significance: translating the science of mesenchymal stem cells into medicine. Nature Medicine. 2013; 19(1):35-42. Tang et al. White fat progenitor cells reside in the adipose vasculature. Science. 2008; 322(5901):583-6. Chan et al. Clonal precursor of bone, cartilage, and hematopoietic niche stromal cells. Proceedings of the National Academy of Sciences of the United States of America. 2013; 110(31):12643-8. Jain. Molecular regulation of vessel maturation. Nature Medicine. 2003; 9(6):685-93. Carmeliet and Jain. Molecular mechanisms and clinical applications of angiogenesis. Nature. 2011; 473(7347):298-307. Huang et al. Embryonic stem cell-derived endothelial cells engraft into the ischemic hindlimb and restore perfusion. Arteriosclerosis, Thrombosis, and Vascular Biology. 2010; 30(5):984-91. Koh et al. Stromal vascular fraction from adipose tissue forms profound vascular network through the dynamic reassembly of blood endothelial cells. Arteriosclerosis, Thrombosis, and Vascular biology. 2011; 31(5):1141-50. Kusuma et al. Self-organized vascular networks from human pluripotent stem cells in a synthetic matrix. Proceedings of the National Academy of Sciences of the United States of America. 2013; 110(31):12601-6.

SUMMARY OF THE INVENTION

Methods, compositions, and kits for producing functional blood vessels, and progenitors thereof are provided. These methods, compositions and kits find use in transplantation, for experimental evaluation, as a source of lineage and cell-specific products, and the like, for example for use in treating human disorders of the vascular system, and in the reconstitution of functional vessels in vivo through co-transplantation with supporting niche stromal cells for treatment of ischemic injury in the peripheral limbs and heart. The cell populations of the invention, when engrafted into a recipient, anastomose with host vasculature and regenerate functional blood vessels. In some embodiments, the cells are mammalian cells. In some embodiments, the cells are human or mouse cells.

It is shown herein that two populations of stromal cells provide de novo vessel formation in vivo. The cells are resident in various stromal cell compartments, including without limitation bone marrow, lung, adipose tissue, etc. The presence of the cells in adult tissue is of particular interest. One population, referred to herein as the P2 population, comprises multipotent cells that generate both vessels and adipose tissue. The other population, referred to herein as the P1 population, provides a stromal signaling role to guide differentiation of the P2 population, including secretion of PDGF. A benefit to the use of these cell populations is the ease of isolation from adipose tissue, e.g. lipoasiprate, and the ability to use freshly isolated cells in the absence of expansion or differentiation in vitro.

For in vivo uses, an engineered cell composition comprising a mixture of P1 and P2 cells can be provided systemically or as a localized implant, e.g. in a matrigel or other suitable matrix. The cells may be provided in a defined ratio and dose. In other embodiments an effective dose of a P2 cell population is provided in combination with an effective dose of growth factors required for vessel formation, including without limitation PDGF. In some aspects of the invention, methods are provided for treating a subject in need of cell transplantation therapy of vascular tissues. In some such embodiments, the subject is contacted with an engineered cell population comprising a mixture of P1 and P2 cells; or P2 cells in combination with growth factors.

The P1 and P2 cells can be isolated from stromal tissue by any convenient method, including, for example, flow cytometry with fluorescence or magnetic tags, and may be isolated to a purity to where the desired cells are, for example at least about 25% of the population; at least about 50% of the population; at least about 75% of the population; at least about 85% of the population, at least about 95% of the population, or more.

A P2 cell population may be characterized as a population of cells present in stromal tissue, including adult stromal tissue, that can give rise to functional vessels and adipose tissue. The surface phenotype is CD45$^-$ Tie2$^+$ CD105$^{high}$ PDGFRα$^+$ CD31$^-$. Cells can be isolated from tissue by positive or negative selection as appropriate for one or more of these markers.

A P1 cell population may be characterized as a population of cells present in stromal tissue, including adult stromal tissue, that supports development of vasculature. The surface phenotype of the cells is CD45$^-$ Tie2$^+$ CD105$^+$ PDGFRα$^-$ CD31$^+$. Cells can be isolated from tissue by positive or negative selection as appropriate for one or more of these markers.

In some embodiments, an engineered cell composition is provided, in which isolated P1 and P2 cell populations are isolated from a tissue source, and combined to provide a regenerative composition. The cells may be combined in a ratio of, for example, P1:P2 of 1:100; 1:50; 1:20; 1:15; 1:10; 1:5; 1:3; 1:2; 1:1; 2:1; 3:1; 5:1; 10:1; 15:1, 20:1; 50:1; 100:1, etc. An effective dose may be at least about $10^4$ cells total, at least about $10^5$ cells total, at least about $10^6$ cells total, at least about $10^7$ cells total, at least about $10^8$ cells total, at least about $10^9$ cells total, at least about $10^{10}$ cells total, or more. In an alternative embodiment the P1 cell population is replaced by factors in an effective dose to stimulate vascular growth by the P2 cell population. In an alternative embodiment a purified cell population is isolated from stromal tissue for markers common to the P1 and P2 cell populations, e.g. a CD45$^-$, Tie2$^+$, CD105$^+$ cell population and utilized for vasculogenesis. Such embodiments include, without limitation, implantation of the cell population(s) in a matrix that serves to localize cells and factors In some embodiments, purified P2 cell populations, which possess adipogenic potential in the absence of P1 cells, are used to generate adipose tissue for soft tissue reconstruction. Stromal cells from patient source can be depleted of P1 cells with P1 specific markers and enriched for P2 cells prior to injection into adipose-deficient areas to form new adipose tissue. Such embodiments include, without limitation, an engineered cell composition comprising P2 cells and antagonistic factors to P1 expressed cytokines that inhibit adipogenesis.

Enrichment of P1 and P2 progenitor populations from adipose tissue followed by direct transplantation is a significant advance over current cell-based methods for treatment of ischemic injury because it has can be applied autologously without in vitro culture, and results in formation of de novo blood vessels, e.g. as autogenous bedside tissue engineering and could be used in the operating room for vascular surgery cases.

The P1 and P2 cell populations are optionally isolated from the individual that is treated. In other embodiments the cells are allogeneic, for example they may be cryopreserved in a bank. Also provided is a package (for example a box, a bottle or a bottle and box) that includes an effective dose of such cells and a package insert or label that indicates that the cells are to be administered in an effective dose to a patient for the generation of vasculature. The packaging optionally further includes suitable reagents for the isolation of human cell populations.

In some aspects of the invention, methods are provided for treating a subject in need of cell transplantation therapy for adipose or vascular tissues, by introducing locally or systemically an engineered cell composition as described herein. In some such embodiments the subject is suffering from an ischemic condition. In some such embodiments the subject is provided with a graft or other prosthetic solid tissue in need of vascularization. In some such embodiments, the subject is contacted with factors and optionally cells using the methods and compositions of the invention. In certain embodiments, the cells are derived from the subject. In some such embodiments the cell composition is provided in a matrix, e.g. a biocompatible and optionally biodedegradable matrix or lattice, e.g. formed from matrigel, polylactic acid, polyglycolic acid, Poly(lactic-co-glycolic acid) (PLGA); collagen, alginate, and the like capable of supporting vasculogenesis in a three dimensional configuration.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1A-1E. Prospective isolation of vasculogenic and adipogenic progenitors from adipose tissue. (FIG. 1A). FACS profile of vessel and adipocyte forming populations defined by differential expression of surface markers including CD45, Ter119, Tie2, CD105, Sca-1, CD31, and PDGFRα. Two major populations P1 (CD45−, Ter119−, Tie2+, CD105+, Sca-1+, PDGFRα−, CD31+) and P2 (CD45−, Ter119−, Tie2+, CD105$^{high}$, Sca-1+, PDGFRα+, CD31−) were identified. (FIG. 1B). Experimental schematic for in vivo cell fate experiments. Briefly, 200,000 fresh P1 and P2 cells were isolated from GFP donors and delivered into the inguinal fat pads of immunodeficient recipients (n=20). P1 (FIG. 1B(i)) was found to form stunted vessels whereas P2 (FIG. 1B(ii)) was found to form both fat cells and stunted vessels. Arrows indicate positive co-staining of oil red and GFP visible in plane. (FIG. 1C). Co-transplantation of P1 and P2 cell populations in vivo yields GFP vessels carrying blood. (FIG. 1D). Perfusion of recipient animals with DyLight 594-lectin demonstrates GFP vessels derived from donor cells are functional and connect with host vasculature. DyLight-594 dye can be clearly seen in lumen of GFP-lined vessel walls. (FIG. 1E). Transplantation of single P1 cell populations from actin-RFP and single P2 cell populations from GFP mice were found to give rise to stunted vessels and stunted vessels/fat respectively. The combination of P1 actin-RFP cells and P2 actin-GFP cells was found to give rise to vessels.

FIG. 2A-2H. Co-transplantation of adipose derived P1 and P2 cell populations functionally rescue ischemic injury. (FIG. 2A). Laser Doppler measurement of restored blood flow in ischemic hindlimbs of Rag2/gamma(c) knockout immunodeficient mice treated with transplanted P1 (CD45−, Ter119−, Tie2+, CD105+, Sca-1+, PDGFRα−, CD31+) and P2 (CD45−, Ter119−, Tie2+, CD105$^{high}$, Sca-1+, PDGFRα+, and CD31−) cell populations isolated from GFP donor mouse adipose tissue. (FIG. 2B). Quantification of re-perfusion demonstrates increased recovery in animals receiving P1 (CD45−, Ter119−, Tie2+, CD105+, Sca-1+, PDGFRα−, CD31+) and P2 (CD45−, Ter119−, Tie2+, CD105$^{high}$, Sca-1+, PDGFRα+, and CD31−) cell treatment at day 7 and day 14 post-injury as compared to control animals. (FIG. 2C). Fluorescence microscopy demonstrates engraftment of GFP donor vessels in the ischemic hindlimb 14 days after transplantation. Peripheral blood is observed to be carried in the GFP vessels via brightfield microscopy (FIG. 2C(i)-2C(ii)). Perfusion of vessels with DyLight 594-lectin demonstrates functionality (FIG. 2C(iii)-2C(iv)). (FIG. 2D). Bioluminescence imaging of recipient immunodeficient Rag2/gamma(c) knockout animals demonstrates engraftment and survival of GFP P1 (CD45−, Ter119−, Tie2+, CD105+, Sca-1+, PDGFRα−, CD31+) and P2 (CD45−, Ter119−, Tie2+, CD105$^{high}$, Sca-1+, PDGFRα+, and CD31−) cells through day 56 post delivery in a murine model of MI. Cell survival is observed to decrease over time. (FIG. 2E(i)-2E(ii)). Perfusion by DyLight 594-lectin (FIG. 2E(i)) in explanted recipient hearts reveals functionality of donor-derived vessels as well as presence of GFP lined vessels that carry peripheral blood (FIG. 2E(ii)). (FIG. 2F(i)-2F(iii)). Immunostaining of GFP P1 (CD45−, Ter119−, Tie2+, CD105+, Sca-1+, PDGFRα−, CD31+) and GFP P2 (CD45−, Ter119−, Tie2+, CD105$^{high}$, Sca-1+, PDGFRα+, and CD31−) cell grafts demonstrates positive staining for markers of pericyte (NG2; FIG. 2F(i)), smooth muscle (SMA; FIG. 2F(ii)), and endothelial (CD31; FIG. 2F(iii)) cell fate. (FIG. 2G). Small animal echocardiography demonstrates improved functional recovery in animals receiving P1 (CD45−, Ter119−, Tie2+, CD105+, Sca-1+, PDGFRα−, CD31+) and P2 (CD45−, Ter119−, Tie2+, CD105$^{high}$, Sca-1+, PDGFRα+, and CD31−) cell treatment as compared to animals receiving vehicle alone or unsorted fat. (FIG. 2H). Quantification of fractional shortening demonstrates improvement in animals receiving P1 (CD45−, Ter119−, Tie2+, CD105+, Sca-1+, PDGFRα−, CD31+) and P2 (CD45−, Ter119−, Tie2+, CD105$^{high}$, Sca-1+, PDGFRα+, and CD31−) cell treatment by week 4 post surgery as compared to animals receiving vehicle alone or unsorted fat. Improved cardiac function is observed through week 8 post surgery. *P<0.05 vs control. Error bars represent SEM.

FIG. 3A-3B(ii). FIG. 3A Cell surface markers of P1 and P2 vessel stem cell populations. P1 (CD45−, Ter119−, Tie2+, CD105+, Sca-1+, PDGFRα−, CD31+) and P2 (CD45−, Ter119−, Tie2+, CD105$^{high}$, Sca-1+, PDGFRα+, and CD31−) cell populations were identified using nine cell surface markers enlisted in the table presented. FIG. 3B FACs plots for P1 (FIG. 3B(i)) and P2 (FIG. 3B(ii)) are presented based on these markers.

FIG. 4A-4C. Confirmation of P1 and P2 stem cell populations in stromal tissues of different organs. FACs analysis of murine bone marrow (FIG. 4A), lung stroma (FIG. 4B), and adipose tissue (FIG. 4C) demonstrates presence of P1 (CD45−, Ter119−, Tie2+, CD105+, Sca-1+, PDGFRα−, CD31+) and P2 (CD45−, Ter119−, Tie2+, CD105$^{high}$, Sca-1+, PDGFRα+, and CD31−) stem cell subpopulations.

(FIG. 5A). Transplantation of GFP positive lung-derived P1 (CD45−, Ter119−, Tie2+, CD105+, Sca-1+, PDGFRα−, CD31+) cells from L2G donor animals into the inguinal fat pads of immunodeficient recipient animals yield stunted vessels after 14 days of in vivo transplantation. (FIG. 5B). Transplantation of GFP positive lung-derived P2 (CD45−, Ter119−, Tie2+, CD105$^{high}$, Sca-1+, PDGFRα+, CD31−) cells from L2G donor animals yield stunted vessels and fat (arrows) after 14 days of in vivo transplantation in the inguinal fat pad of immunodeficient animals.

FIG. 7A-7C), endothelial (CD31; FIG. 7D-7F), or pericyte (NG2; FIG. 7G-7I) origin.

(FIG. 8A). Isolation and FACs characterization of P1 (CD45−, Tie2+, PDGFRα−, CD31+) and P2 (CD45−, Tie2+, PDGFRα+, and CD31−) cell populations within human lipoaspirate. (FIG. 8B). Transplantation of human P1 and P2 cell populations into murine ischemic hindlimb model demonstrates improved re-vascularization in the injured hindlimb (yellow box) as compared to treatment with animals treated with Matrigel only. (FIG. 8C(i)-8C(iii)). Explant of human P1 and P2 cell grafts marked via GFP lentivirus demonstrates GFP donor vessels (FIG. 8C(i)) co-stained with human-specific CD31 (FIG. 8C(ii)-8C(iii)).

FIG. 9A-9D. Vessel forming clones are amplified in response to ischemia in Actin Cre x rainbow mice. The top panel (FIG. 9A) shows non-femoral artery ligation control and bottom panel (FIG. 9B) shows clonal expansion of vessel forming populations as imaged by confocal microscopy. Bottom left diagram (FIG. 9C) shows experimental scheme. Bottom right tables (FIG. 9D) show quantification of clonal amplification in top vs bottom panels by Amaris software.

DETAILED DESCRIPTION OF THE EMBODIMENTS OF THE INVENTION

Figure 3A:
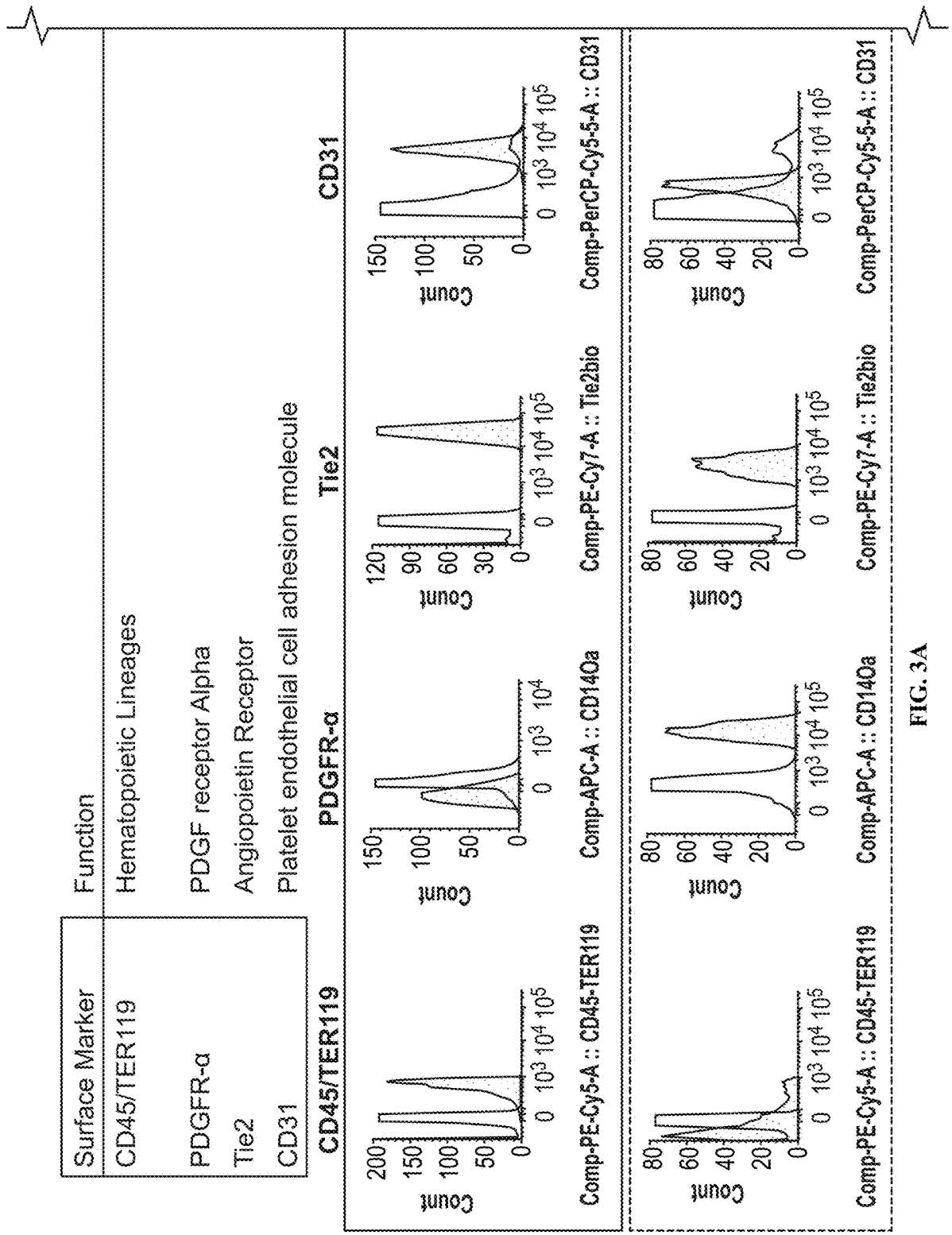

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Methods, compositions and kits for producing functional blood vessels thereof are provided. These methods, compositions and kits find use in transplantation, for experimental evaluation, as a source of lineage and cell-specific products, and the like, for example for use in treating human disorders requiring formation of vessels.

These and other objects, advantages, and features of the invention will become apparent to those persons skilled in the art upon reading the details of the subject methods and compositions as more fully described below.

General methods in molecular and cellular biochemistry can be found in such standard textbooks as Molecular Cloning: A Laboratory Manual, 3rd Ed. (Sambrook et al., Harbor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and Clon-Tech.

By "proliferate" it is meant to divide by mitosis, i.e. undergo mitosis. An "expanded population" is a population of cells that has proliferated, i.e. undergone mitosis, such that the expanded population has an increase in cell number, that is, a greater number of cells, than the population at the outset.

The term "explant" refers to a portion of an organ or tissue therein taken from the body and cultured in an artificial medium. Cells that are grown "ex vivo" are cells that are taken from the body in this manner, temporarily cultured in vitro, and returned to the body.

The term "primary culture" denotes a mixed cell population of cells from an organ or tissue within an organ. The word "primary" takes its usual meaning in the art of tissue culture. Primary tissue, or primary tissue derived cells refers to cells that have not been expanded or maintained in culture.

The term "tissue" refers to a group or layer of similarly specialized cells which together perform certain special functions.

The term "organ" refers to two or more adjacent layers of tissue, which layers of tissue maintain some form of cell-cell and/or cell-matrix interaction to form a microarchitecture.

The terms "individual," "subject," "host," and "patient," are used interchangeably herein and refer to any mammalian subject for whom diagnosis, treatment, or therapy is desired, particularly humans.

The terms "treatment", "treating", "treat" and the like are used herein to generally refer to obtaining a desired pharmacologic and/or physiologic effect. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a mammal, particularly a human, and includes: (a) preventing the disease or symptom from occurring in a subject which may be predisposed to the disease or symptom but has not yet been diagnosed as having it; (b) inhibiting the disease symptom, i.e., arresting its development; or (c) relieving the disease symptom, i.e., causing regression of the disease or symptom.

"Co-administer" means to administer in conjunction with one another, together, coordinately, including simultaneous or sequential administration of two or more agents.

"Comprising" means, without other limitation, including the referent, necessarily, without any qualification or exclusion on what else may be included. For example, "a composition comprising x and y" encompasses any composition that contains x and y, no matter what other components may be present in the composition. Likewise, "a method comprising the step of x" encompasses any method in which x is carried out, whether x is the only step in the method or it is only one of the steps, no matter how many other steps there may be and no matter how simple or complex x is in comparison to them. "Comprised of" and similar phrases using words of the root "comprise" are used herein as synonyms of "comprising" and have the same meaning. The methods of the invention also include the use of factor combinations that consist, or consist essentially of the desired factors.

"Effective amount" generally means an amount which provides the desired local or systemic effect. For example, an effective amount is an amount sufficient to effectuate a beneficial or desired clinical result. The effective amounts can be provided all at once in a single administration or in fractional amounts that provide the effective amount in several administrations. The precise determination of what would be considered an effective amount may be based on factors individual to each subject, including their size, age, injury, and/or disease or injury being treated, and amount of time since the injury occurred or the disease began. One skilled in the art will be able to determine the effective amount for a given subject based on these considerations which are routine in the art. As used herein, "effective dose" means the same as "effective amount."

The term "progenitor cell" as used herein refers to a cell population that generates at least one differentiated progenitor, and may give rise to multiple lineages. Progenitor cells may self-renew, i.e. when the cells undergo mitosis, they produce at least one daughter cell that is a progenitor cell, although typically the self-renewal is of limited duration relative to stem cells. The cells are not pluripotent, that is, they are not capable of giving rise to cells of other organs in vivo.

Human and mouse P1 and P2 cells share a common phenotype. A P2 cell population may be characterized as a population of cells present in stromal tissue, including adult stromal tissue, that can give rise to functional vessels and adipose tissue. The surface phenotype is $CD45^-$ $Tie2^+$ $CD105^{high}$ $PDGFR\alpha^+$ $CD31^-$. Cells can be isolated from tissue by positive or negative selection as appropriate for one or more of these markers. A P1 cell population may be characterized as a population of cells present in stromal tissue, including adult stromal tissue, that supports development of vasculature. The surface phenotype of the cells is $CD45^-$ $Tie2^+$ $CD105^+$ $PDGFR\alpha^-$ $CD31^+$. Cells can be isolated from tissue by positive or negative selection as appropriate for one or more of these markers.

Adipose-Derived Cells. Adipose-derived cells refer to cells that originate from adipose tissue. By "adipose" is meant any fat tissue. The adipose tissue may be brown or white adipose tissue, derived from subcutaneous, omental/visceral, mammary, gonadal, or other adipose tissue site. Preferably, the adipose is subcutaneous white adipose tissue. The adipose tissue may be from any organism having fat tissue. Preferably, the adipose tissue is mammalian, most preferably the adipose tissue is human. A convenient source of adipose tissue is from liposuction surgery, however, the source of adipose tissue or the method of isolation of adipose tissue is not critical to the invention.

Adipose tissue offers many practical advantages for tissue engineering applications. It is abundant and accessible to harvest methods with minimal risk to the patient. It is estimated that there are more than $10^4$ stem cells per gram of adipose tissue (Sen et al 2001, Journal of Cellular Biochemistry 81:312-319), which cells can be used immediately or cryopreserved for future autologous or allogeneic applications.

Methods for the isolation, expansion, and differentiation of human adipose tissue-derived cells have been reported. See for example, Burris et al 1999, Mol Endocrinol 13:410-7; Erickson et al 2002, Biochem Biophys Res Commun. Jan. 18, 2002; 290(2):763-9; Gronthos et al 2001, Journal of Cellular Physiology, 189:54-63; Halvorsen et al 2001, Metabolism 50:407-413; Halvorsen et al 2001, Tissue Eng. 7(6):729-41; Harp et al 2001, Biochem Biophys Res Commun 281:907-912; Saladin et al 1999, Cell Growth & Diff 10:43-48; Sen et al 2001, Journal of Cellular Biochemistry 81:312-319; Zhou et al 1999, Biotechnol. Techniques 13: 513-517. Adipose tissue-derived stromal cells may be obtained from minced human adipose tissue by collagenase digestion and differential centrifugation [Halvorsen et al 2001, Metabolism 50:407-413; Hauner et al 1989, J Clin Invest 84:1663-1670; Rodbell et al 1966. J Biol Chem 241:130-139].

For isolation of cells from tissue, an appropriate solution may be used for dispersion or suspension. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc.

The cell population may be used immediately. Alternatively, the cell population may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

"PDGF", Platelet-derived growth factor, is one of the numerous growth factors, or proteins that regulate cell growth and division. In particular, it plays a significant role in angiogenesis, which is the growth of blood vessels from already-existing blood vessel tissue. It does so by recruiting perivascular cells to the immature tumor vasculature where they interact with endothelial cells to stabilize the vessels resulting in mature blood vessels (Andrae et al. (2008), Genes and Development 22, pp. 1276-1312).

There are at least four members of the PDGF family of proteins that regulate the PDGF signaling pathway, specifically PDGF-A, PDGF-B, PDGF-C, and PDGF-D. These four PDGFs assemble into disulfide-linked dimers via homo- or heterodimerization. At least five different dimeric isoforms of PDGF have been described to date and include PDGF-AA, PDGF-BB, PDGF-CC, PDGF-DD, and PDGF-AB, all of which bind to PDGF receptors (PDGFRs) to activate the PDGF signaling pathway.

There are at least two identified PDGFRs, PDGFR-$\alpha$ and PDGFR-$\beta$. Each PDGFR has an extracellular region, a transmembrane domain, and an intracellular region having intracellular tyrosine kinase activity. PDGFRs can dimerize to form the homodimers PDGFR-$\alpha$/PDGFR-$\alpha$ or PDGFR-$\beta$/PDGFR-$\beta$ and the heterodimer PDGFR-$\alpha$/PDGFR-$\beta$. Each of these PDGFR dimer forms recognize different dimeric isoforms of PDGF. For example, PDGFR-$\alpha$/PDGFR-$\alpha$ recognizes PDGF-AA, AB, BB and CC ligands, PDGFR-$\alpha$/PDGFR-$\beta$ recognizes PDGF-AB, BB, CC, and DD, and PDGFR-$\beta$/PDGFR-$\beta$ recognizes PDGF-BB and DD. Deletion mutagenesis of the PDGF-AA and -BB binding sites have been mapped to amino acids 1-314 of PDGFR-$\alpha$ while the PDGF-BB binding sites have been mapped to amino acids 1-315 of PDGFR-$\beta$. The extracellular region of these PDGFRs, which mediate binding to PDGFs contain five immunoglobulin (Ig)-like domains, each ranging from about 88 to about 114 amino acids in length. See Lokker et al., J Biol. Chem., 1997, 272(52): 33037-44, Miyazawa et al., J Biol. Chem., 1998, 273(39): 25495-502; and Mahadevan et al., J Biol. Chem., 1995, 270(46):27595-600, which are incorporated herein by reference their entirety. The nature of the receptor binding specificities of VEGF-A and PDGF-B allow targeting to multiple forms of VEGFR and PDGFR (VEGFR1, VEGFR2, PDGFR-$\alpha$, and PDGFR-$\beta$), respectively.

Tissue engineering is the use of a combination of cells, engineering and materials methods, and suitable biochemical and physico-chemical factors to improve or replace biological functions. Cells may be implanted or 'seeded' into an artificial structure capable of supporting three-dimensional tissue formation. These structures, referred to herein as a matrix or scaffold, allow cell attachment and migration, deliver and retain cells and biochemical factors, enable diffusion of vital cell nutrients and expressed products. A high porosity and an adequate pore size are necessary to facilitate cell seeding and diffusion throughout the whole structure of both cells and nutrients. Biodegradability is often a factor since scaffolds may be absorbed by the surrounding tissues without the necessity of a surgical removal. The rate at which degradation occurs has to coincide as much as possible with the rate of tissue formation: this means that while cells are fabricating their own natural matrix structure around themselves, the scaffold is able to provide structural integrity within the body and eventually it will break down leaving the neotissue, newly formed tissue which will take over the mechanical load. Injectability is also important for clinical uses.

In some embodiments tissue is engineered to generate vasculature. In other embodiments tissue is engineered to generate adipose tissue, e.g. for therapeutic or cosmetic purposes.

Many different materials (natural and synthetic, biodegradable and permanent) have been investigated, e.g. Puramatrix, polylactic acid (PLA), polyglycolic acid (PGA) and polycaprolactone (PCL), and combinations thereof. Scaffolds may also be constructed from natural materials, e.g. proteins such as collagen, fibrin, etc; polysaccharidic materials, such aschitosan; alginate, glycosaminoglycans (GAGs) such as hyaluronic acid, etc. Functionalized groups of scaffolds may be useful in the delivery of small molecules (drugs) to specific tissues. Another form of scaffold under investigation is decellularised tissue extracts whereby the remaining cellular remnants/extracellular matrices act as the scaffold.

A system for pharmaceutical use, i.e. a scaffold or implant with cells and/or factors, can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the NR pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

A cell transplant, as used herein, is the transplantation of one or more cells into a recipient body, usually for the purpose of augmenting function of an organ or tissue in the recipient. As used herein, a recipient is an individual to whom tissue or cells from another individual (donor), commonly of the same species, has been transferred. Generally the MHC antigens, which may be Class I or Class II, will be matched, although one or more of the MHC antigens may be different in the donor as compared to the recipient. The graft recipient and donor are generally mammals, preferably human. Laboratory animals, such as rodents, e.g. mice, rats, etc. are of interest for drug screening, elucidation of developmental pathways, etc. For the purposes of the invention, the cells may be allogeneic, autologous, or xenogeneic with respect to the recipient.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical composition, i.e. combinations of cells, which may be provided in a matrix, can be administered for therapeutic purposes. Toxicity and therapeutic efficacy of the cells can be determined according to standard pharmaceutical procedures in cell cultures and/or experimental animals. The data obtained from cell culture and/or animal studies can be used in formulating a range of dosages for humans.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxin, which may be present during the synthesis or purification process. Compositions for parental administration are also sterile, substantially isotonic and made under GMP conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Mammalian species that may be treated with the present methods include canines and felines; equines; bovines; ovines; etc. and primates, particularly humans. Animal models, particularly small mammals, e.g. murine, lagomorpha, etc. may be used for experimental investigations.

More particularly, the present invention finds use in the treatment of subjects, such as human patients, in need of vasculogenic therapy. Examples of such subjects would be subjects suffering from conditions associated with ischemic conditions, genetic defects, disease, organ transplant, etc. Patients having diseases and disorders characterized by such conditions will benefit greatly by a treatment protocol of the pending claimed invention.

Blood vessels that carry oxygen, nutrients, cells and signals are critical in both developmental and adult physiology. Without sufficient blood supply, tissues and organs cannot maintain regular activities. Induction of neovasculature provides a strategy to treat many ischemic illnesses, especially cardiovascular diseases (CVDs) including coronary and peripheral arterial diseases. An estimated 82,600,000 American adults (≥20 years old) have one or more types of CVDs; CVDs caused 813,804 of all 2,243,712 deaths (33.6%) or one of every 2.9 deaths in 2007, and coronary heart disease caused approximately one of every six deaths. The direct and indirect cost of CVD was estimated to be US $286 billion in 2007. Therapy to engraft the cell populations of the invention find use to revascularize ischemic tissues, including ischemic heart.

Depending on the organs affected, CVD can be classified into coronary artery disease, cerebrovascular disease, peripheral arterial disease and aortic (thoracic or abdominal) atherosclerosis. Ischemic heart disease and peripheral arterial disease (PAD) are of particular interest. CVD is generally characterized by narrowing or occlusion of the blood supply of these vascular beds, and is most commonly caused by atherosclerosis. Treatment options for CVD generally aim to re-establish blood flow through the affected vascular beds, and are administered based on the severity of the disease. In cases of acute disease or full vascular occlusion, vascular stents may be used to expand vessels when one or a few vessels are affected, while surgical bypass is necessary when multiple vascular beds are occluded. Despite the set of currently available treatment options for patients with CVD, there is a subset of patients with advanced disease for whom surgical revascularization is not an option due to the existence of various co-morbidities that prohibit them from undergoing surgical procedures. Therapeutic angiogenesis stimulates the growth of new blood vessels in order to re-supply blood flow to affected ischemic tissues.

There are several mechanisms by which blood vessel formation occurs including vasculogenesis, angiogenesis, and arteriogenesis. The earliest blood vessel formation in a developing embryo arises via vasculogenesis, in which endothelial progenitor cells coalesce to form solid cords. These initially lumenless cords then transform into patent vessels in the process of tubulogenesis. Unlike the de novo blood vessel formation process associated with vasculogenesis, angiogenesis is defined as sprouting new blood vessels from pre-existing blood vessel networks and is important for expanding the vascular bed initially formed via vasculogenesis. Arteriogenesis is the maturation of arterio-arteriolar anastomoses by the recruitment and coating of pre-formed vessels with pericytes or vascular smooth muscle cells.

An effective amount of a pharmaceutical composition of the invention for vascular generation is the amount that will result in an increase the number of functional blood vessels at the site of implant, and/or will result in measurable reduction in the rate of disease progression in vivo. For example, an effective amount of a pharmaceutical composition will increase blood circulation in a targeted tissue by at least about 5%, at least about 10%, at least about 20%, preferably from about 20% to about 50%, and even more preferably, by greater than 50% (e.g., from about 50% to about 100%) as compared to the appropriate control, the control typically being a subject not treated with the composition.

The methods of the present invention also find use in combined therapies, e.g. in with therapies that are already known in the art to provide relief from symptoms associated with the aforementioned diseases, disorders and conditions. The combined use of a pharmaceutical composition of the present invention and these other agents may have the advantages that the required dosages for the individual drugs is lower, and the effect of the different drugs complementary.

In some embodiments an effective dose of P2 and P1 cells are provided in an implant or scaffold for the de novo generation of blood vessels. An effective cell dose may depend on the purity of the population. In some embodiments an effective dose delivers a P1 and P2 dose of at least about $10^2$, about $10^3$, about $10^4$, about $10^5$, about $10^6$, about $10^7$, about $10^8$, about $10^9$ or more cells, which cells may be present in the cell population at a concentration of about 1%, about 5%, about 10%, about 20%, about 30%, about 40%, about 50%, about 60%, about 70%, about 80%, about 90% or more.

Adipose tissue engineering (TE) is a growing field that addresses current clinical needs related to various adipose tissue pathologies and defects. Soft tissue replacement is often required when disease, trauma, or injury damages adipose tissue in various areas of the body. Soft tissue defects not only affect patients cosmetically, but also affect the emotional well-being of patients and may impair function. There is, therefore, a strong clinical need for adipose tissue substitutes. Currently, for breast tissue specifically, clinicians perform surgeries using autologous tissue flaps or commercially available fillers such as fibrin, hyaluronic acid, and viscoelastic hylan gels. Although these methods offer a degree of clinical success, these techniques still have significant pitfalls for both surgeons and patients, such as volume loss and donor-site morbidity over time. The field of tissue engineering provides strategies in which engineered tissue is tailored to a specific site. Tissue engineering strategies incorporate P1 cell populations, biomaterial scaffolds, and a microenvironment to provide the appropriate cues and signals for growth and tissue formation. Soft tissue replacement therapies are often required after tumor resection or trauma, or as the result of congenital abnormalities.

Many biomaterials have been explored for adipose tissue engineering. Both synthetic and natural polymers have been utilized extensively for adipose tissue engineering studies. Considerable advantages and disadvantages with respect to material biocompatibility, mechanical and chemical properties, and degradability for soft tissue applications have been reported. For soft tissue applications, considerable work has been performed using polymers such as poly(lactic acid) (PLA), poly(glycolic acid) (PGA), and the copolymer poly(lactic-co-glycolic acid) (PLGA). These polymers degrade by acid hydrolysis into lactic and glycolic acids, and their degradability can be controlled by altering the molecular weight, crystallinity, and the ratio of lactic to glycolic acid subunits. Alternatively the use of naturally occurring materials for tissue engineering applications poses advantages with respect to biocompatibility, and their mechanical and biological properties tend to match those found in vivo. There are numerous polymers derived from native ECM that have been utilized for adipose tissue engineering, e.g. collagen, silk fibroin, adipose-derived ECM, fibrin, gelatin, matrigel, etc.

In some embodiments an effective dose of P2 cells are provided in an implant or scaffold for the generation of adipose tissue. An effective cell dose may depend on the purity of the population. In some embodiments an effective dose delivers a P1 dose of at least about $10^2$, about $10^3$, about $10^4$, about $10^5$, about $10^6$, about $10^7$, about $10^8$, about $10^9$ or more cells, which cells may be present in the cell population at a concentration of about 1%, about 5%, about 10%, about 20%, about 30%, about 40%, about 50%, about 60%, about 70%, about 80%, about 90% or more.

METHODS OF THE INVENTION

Vasculogenic cells populations described here may be used in cell replacement or cell transplantation therapy to treat diseases, particularly cardiovascular diseases. Specifically, the cells may be transferred to subjects suffering from a wide range of diseases or disorders that benefit from therapeutic growth of blood vessels.

The cells or a sub-population of cells are purified or isolated from a tissue source prior to transferring to the subject. In other words, one or more steps may be executed to enrich for the cells or a subpopulation of cells, i.e. to provide an enriched population of cells or subpopulation of cells. In some cases, one or more antibodies specific for a marker of P1 or P2 cells are incubated with the cell population and those bound cells are isolated. By a marker it is meant that the marker is selectively expressed, either positively or negatively, by the cells of interest. As is common in the art, a combination of positive and negative selectable markers are used. It will be understood by those of skill in the art that the stated expression levels reflect detectable amounts of the marker protein on or in the cell. A cell that is negative for staining (the level of binding of a marker-specific reagent is not detectably different from an isotype matched control) may still express minor amounts of the marker. And while it is commonplace in the art to refer to cells as "positive" or "negative" for a particular marker, actual expression levels are a quantitative trait. The number of molecules on the cell surface can vary by several logs, yet still be characterized as "positive".

Cells of interest, i.e. cells expressing the marker of choice, may be enriched for, that is, separated from the rest of the cell population, by a number of methods that are well known in the art. For example, flow cytometry, e.g. fluorescence activated cell sorting (FACS), may be used to separate the cell population based on the intrinsic fluorescence of the marker, or the binding of the marker to a specific fluorescent reagent, e.g. a fluorophor-conjugated antibody, as well as other parameters such as cell size and light scatter. In other words, selection of the cells may be effected by flow cytometry Although the absolute level of staining may differ with a particular fluorochrome and reagent preparation, the data can be normalized to a control. To normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining above the brightness of an isotype matched control, but are not as intense as the most brightly staining cells normally found in the population. An alternative control may utilize a substrate having a defined density of marker on its surface, for example a fabricated bead or cell line, which provides the positive control for intensity.

For isolation of cells from tissue, an appropriate solution may be used for dispersion or suspension. Such solution will generally be a balanced salt solution, e.g. normal saline, PBS, Hanks balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The tissue may be enzymatically and/or mechanically dissociated. In some embodiments the vessel tissue is treated with a gentle protease, e.g. dispase, etc., for a period of time sufficient to dissociate the cells, then is gently mechanically dissociated.

An initial separation may select for cells by various methods known in the art, including elutriation, Ficoll-Hypaque or flow cytometry using the parameters of forward and obtuse scatter.

Separation of the subject cell population will then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (propidium iodide, 7-AAD). Any technique may be employed which is not unduly detrimental to the viability of the selected cells.

The affinity reagents may be specific receptors or ligands for the cell surface molecules indicated above. Of particular interest is the use of antibodies as affinity reagents. The details of the preparation of antibodies and their suitability for use as specific binding members are well known to those skilled in the art. Depending on the specific population of cells to be selected, one or more antibodies having specificity for CD45, Tie2, PDGFR, CD105 and CD31 are contacted with the starting population of cells.

As is known in the art, the antibodies will be selected to have specificity for the relevant species, i.e. antibodies specific for human markers are used for selection of human cells; antibodies specific for mouse markers are used in the selection of mouse cells, and the like.

Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium which maintains the viability of the cells. A preferred medium is phosphate buffered saline containing from 0.1 to 0.5% BSA. Various media are commercially available and may be used according to the nature of the cells, including Dulbeccos Modified Eagle Medium (dMEM), Hank's Basic Salt Solution (HBSS), Dulbeccos phosphate buffered saline (dPBS), RPMI, Iscoves medium, PBS with 5 mM EDTA, etc., frequently supplemented with fetal calf serum, BSA, HSA, etc.

The labeled cells are then separated as to the phenotype described above. The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscoves medium, etc., frequently supplemented with fetal calf serum.

Compositions highly enriched for vessel progenitor activity are achieved in this manner. Populations that are enriched by selecting for the expression of one or more markers will usually have at least about 50%, at least about 80% cells of the selected phenotype, at least 90% cells, at least about 95% of the cells, or more, of the selected phenotype. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. Once thawed, the cells are optionally expanded by use of growth factors and/or stromal cells for proliferation and differentiation.

The present methods are useful in the development of an in vitro or in vivo model for vessel function and are also useful in experimentation on gene therapy and for artificial organ construction. The developing vessels serve as a valuable source of novel growth factors and pharmaceuticals and for the production of viruses or vaccines, for in vitro toxicity and metabolism testing of drugs and industrial compounds, for gene therapy experimentation, for the construction of artificial transplantable vessels, and for vessel mutagenesis and carcinogenesis In addition to the transplantation methods described above, cells isolated from tissue, or induced by the methods described above in vitro may be used as a basic research or drug discovery tool, for example to evaluate the phenotype of a genetic disease, e.g. to better understand the etiology of the disease, to identify target proteins for therapeutic treatment, to identify candidate agents with disease-modifying activity, e.g. to identify an agent that will be efficacious in treating the subject. For example, a candidate agent may be added to a cell culture comprising any of the vasculogenic progenitor cells described herein, and the effect of the candidate agent assessed by monitoring output parameters such as survival, the ability to form vessels, and the like, by methods described herein and in the art.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Candidate agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

Candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof. Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Candidate agents are screened for biological activity by adding the agent to one or a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

The methods described herein also provide a useful system for screening candidate agents for activity in modulating cell conversion into cells of a vasculogenic or chondrogenic lineage, e.g. chondrocytes, osteoblasts, or progenitor cells thereof. In screening assays for biologically active agents, cells, usually cultures of cells, are contacted with a candidate agent of interest in the presence of the cell reprogramming or differentiation system or an incomplete cell reprogramming or differentiation system, and the effect of the candidate agent is assessed by monitoring output parameters such as the level of expression of genes specific for the desired cell type, as is known in the art, or the ability of the cells that are induced to function like the desired cell type; etc. as is known in the art.

The features and advantages of the present invention will be more clearly understood by reference to the following examples, which are not to be construed as limiting the invention.

EXPERIMENTAL

Example 1

Formation of De Novo Blood Vessels by a Novel Multipotent Vessel Progenitor Cell Population for Treatment of Ischemic Injury In this brief report, we utilize prospective cell sorting and lineage tracing to identify a novel multipotent CD45− Tie2+ CD105$^{high}$ PDGFRα+ CD31− stem cell population derived from stromal tissue that gives rise to both adipose and vessel cell fates. We demonstrate the co-transplantation of this cell population with supporting niche stromal cells to generate de novo functional vessels in vivo for rescue of ischemic injury.

Results and Discussion

Previous studies assessing cell fate of progenitor cell populations arising from the mesenchyme have utilized lineage tracing and transgenic animal models to demonstrate the existence of lineage-committed progenitor cells in connective tissue. Here we employed an alternative approach based on prospective separation of MSC subfractions via flow cytometry followed by in vivo transplantation for assessment of cell fate. Utilizing this approach, donor MSCs were derived from L2G mice, which co-express firefly luciferase-GFP in every cell of the body. Donor MSCs were stained directly after harvest for a panel of cell surface markers (FIG. 3) and separated into distinct subfractions using fluorescence activated cell sorting (FACs). Our analysis and choice of surface markers was informed by previous work assessing MSC fate. Isolated cell sub-populations were transplanted after FACs into the inguinal fat pads of immunodeficient rag-2/gamma(c) knockout mice and tracked in vivo by bioluminescence imaging for 30 days at which point GFP grafts were explanted for assessment of cell fate.

Our screening and transplantation experiments indicated the presence of a CD45− Tie2+ CD105+ PDGFRα− CD31+ cell population that formed stunted vessels in vivo (P1) and a CD45− Tie2+ CD105$^{high}$ PDGFRα+ CD31− MSC sub-population that formed both vessels and adipose tissue (P2) as confirmed by fluorescence microscopy and oil red staining (FIG. 1A-1B). Assessment of a variety of tissues with stromal cell compartments including bone marrow, lung tissue, and adipose tissue indicated the presence of these two cell populations in all tissues examined (FIG. 4). Of the tissues characterized, adipose tissue was the most easily accessible and clinically relevant for cell analysis. Thus, our subsequent experiments primarily focused on the use of adipose-derived cells.

Figure 5A:
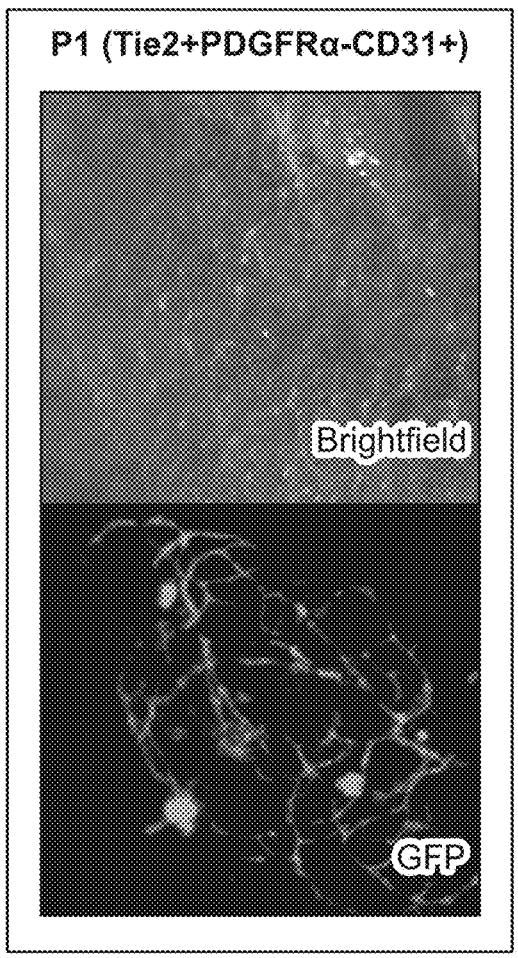
FIG. 5A-5B. Cell fate of lung-derived P1 and P2 stem cell populations following in vivo transplantation.
Figure 5B:
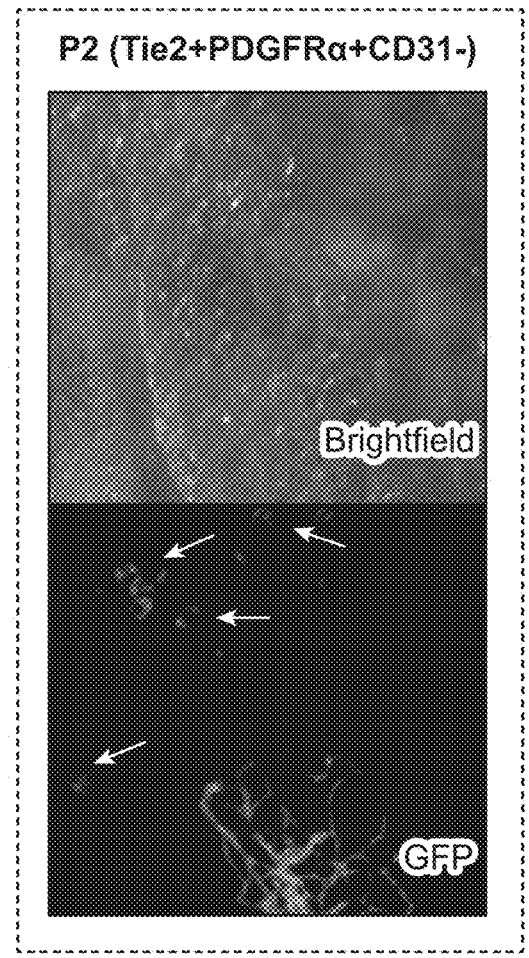

Previous studies have identified the existence of adipose-derived progenitor cells expressing PDGFRβ+ in the stromal vascular fraction (SVF) of adipose tissue. To confirm the fat tissue observed in our GFP grafts was derived from CD45− Tie2+ CD105+ PDGFRα+ CD31− donor cells and not the result of contaminating adipose tissue, we harvested the same population of cells from L2G donor mouse lungs, which are relatively fat absent. CD45− Tie2+ CD105$^{high}$ PDGFRα+ CD31− (P2) stromal cells from the lung gave rise to fat and vessel structures in an identical manner to adipose-derived counterparts when transplanted into the inguinal fat pads of recipient animals (FIG. 5A). By comparison, transplantation of CD45− Tie2+ CD105+ PDGFRα− CD31+ (P1) cells from the SVF of lung tissue were found to give rise only to stunted vessels and did not form adipose tissue (FIG. 5B). Taken together, these results suggest the P2 CD45− Tie2+ CD105+ PDGFRα$^{high}$ CD31− subfraction of stromal tissue is a multipotent source for fat and vessel cells across multiple tissue types.

To better understand the relationship between the P1 CD45− Tie2+ CD105+ PDGFRα− CD31+ and P2 CD45− Tie2+ CD105$^{high}$ PDGFRα+ CD31− stromal subfractions, we isolated both populations from the adipose tissue of donor L2G mice and co-transplanted 1×10$^5$ of each cell type into the inguinal fat pads of immunodeficient rag-2/gamma (c) knockout mice. GFP grafts were explanted 30 days after injection. Surprisingly, grafts derived from co-transplantation of both populations were primarily found to contain vessel structures with minimal presence of adipose cells (FIG. 1C). Retro-orbital perfusion of animals with a DyLight 594 lectin dye specific to endothelial lining showed DyLight 594 lectin dye binding within host and GFP vessels, demonstrating donor cell-derived vessels were connected to host vasculature (FIG. 1D).

Because it was unclear whether the functional vessels observed following stromal subfractionation arose from the P1 CD45− Tie2+ CD105+ PDGFRα− CD31+ or P2 CD45− Tie2+ CD105$^{high}$ PDGFRα+ CD31− donor populations, we next isolated individual cell subpopulations from actin-GFP and actin-RFP reporter mice which express either GFP or RFP in all cells of the body. Single populations of actin-RFP P1 CD45− Tie2+ CD105+ PDGFRα− CD31+ cells derived from actin-RFP mice formed stunted vessels, whereas P2 CD45− Tie2+ CD105$^{high}$ PDGFRα+ CD31− cells derived from actin-GFP mice were found to form both fat and vessels as previously demonstrated. By comparison, co-transplantation of RFP P1 CD45− Tie2+ CD105+ PDGFRα−CD31+ cells with GFP P2 CD45− Tie2+ CD105$^{high}$ PDGFRα+ CD31− into the inguinal fat pads of immunodeficient Rag2/gamma(c) knockout mice gave rise to functional vessels of both colors and minimal fat (FIG. 1E). These findings suggested a stromal signaling role for P1 CD45− Tie2+ CD105+ PDGFRα− CD31+ cells that guides cell fate of the P2 CD45− Tie2+ CD105$^{high}$ PDGFRα+ CD31− progenitor population.

Figure 6:
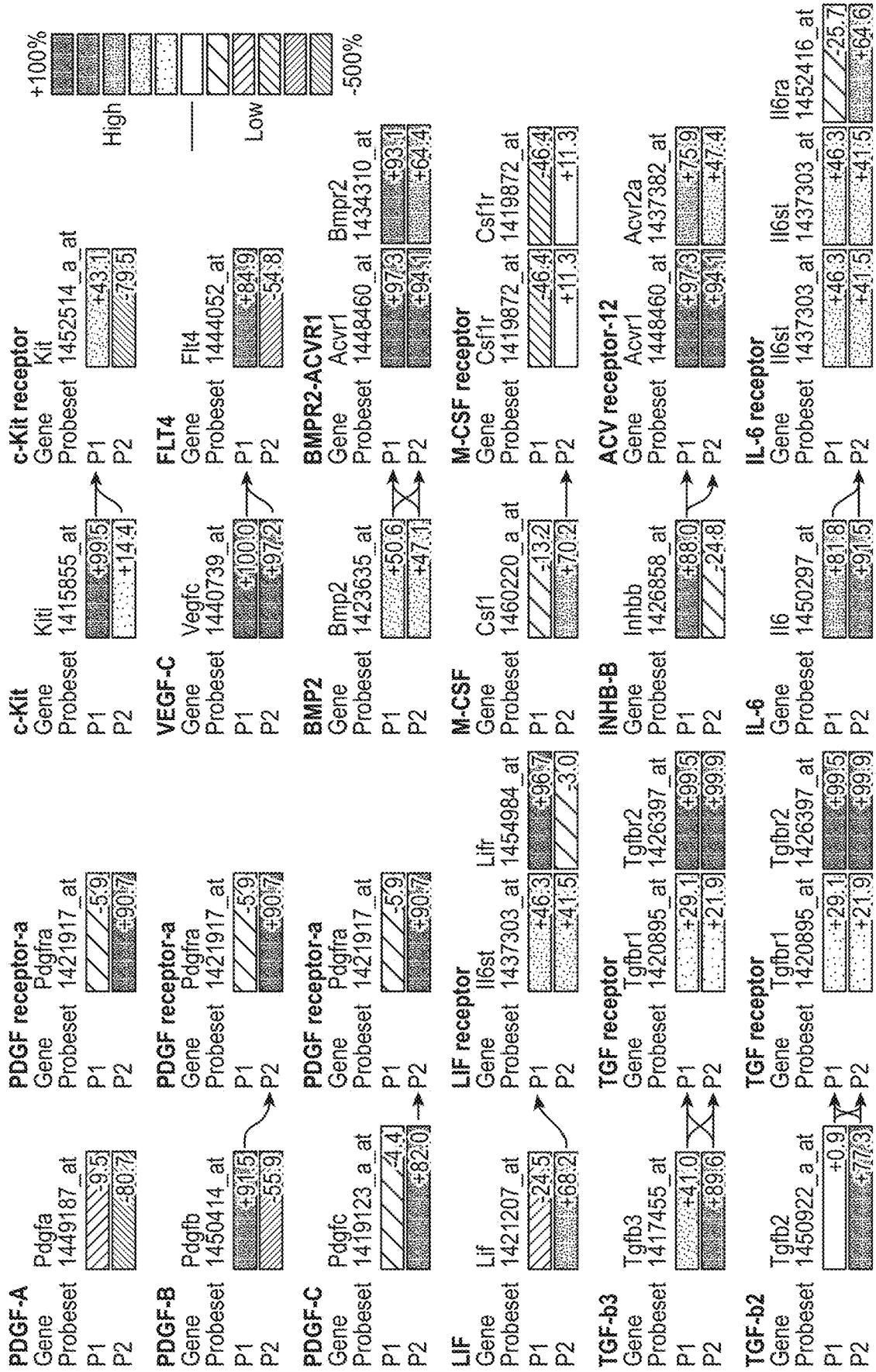
FIG. 6. Gene expression characterization of P1 and P2 stem cell sub-populations. Systematic microarray gene expression characterization of adipose and lung-derived P1 (CD45−, Ter119−, Tie2+, CD105+, Sca-1+, PDGFRα−, CD31+) and P2 (CD45−, Ter119−, Tie2+, CD105$^{high}$, Sca-1+, PDGFRα+, and CD31−) cell populations demonstrates differential expression of vasculogenic factors and their cognate receptors in distinct vessel subsets by using Gene Expression Commons algorithm.
Figure 7C:
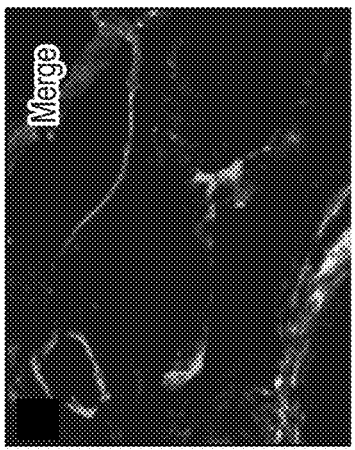
FIG. 7A-7I. PDGF blockade interrupts cell fate signaling between P1 and P2 vessel stem cell subpopulations. Co-injection of GFP P1 (CD45−, Ter119−, Tie2+, CD105+, Sca-1+, PDGFRα−, CD31+) and GFP P2 (CD45−, Ter119−, Tie2+, CD105$^{high}$, Sca-1+, PDGFRα+, and CD31−) cell populations into the fat pad of immunodeficient murine recipients with a saturating dose of PDGRFR antagonist resulted in GFP grafts that did not stain positive for vessel markers including smooth muscle (SMA.
Figure 7F:
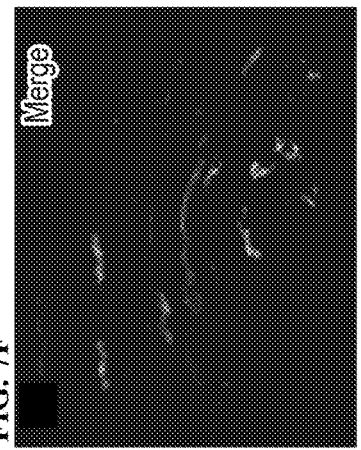
Figure 7I:
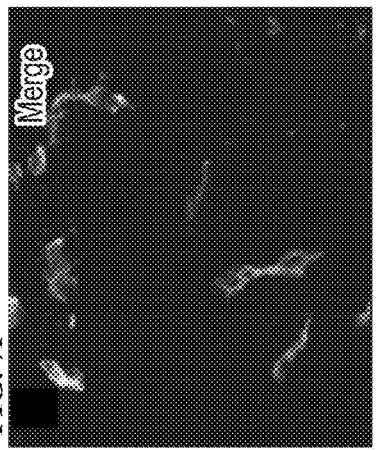
Figure 7B:
Figure 7E:
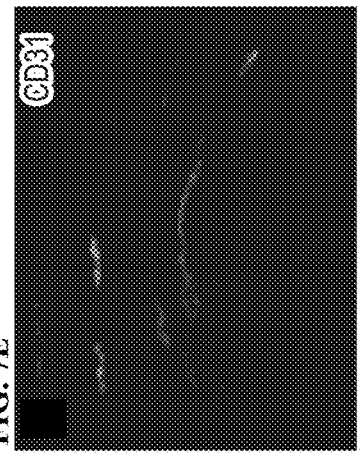
Figure 7H:
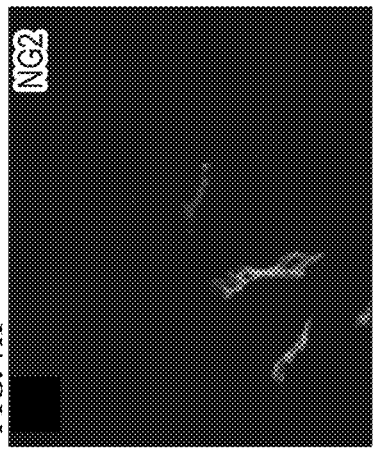
Figure 7A:
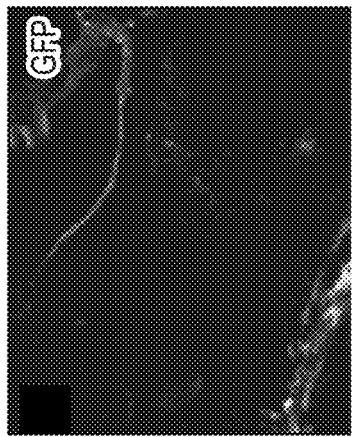
Figure 7D:
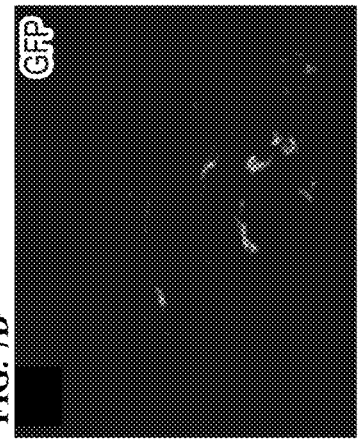
Figure 7G:
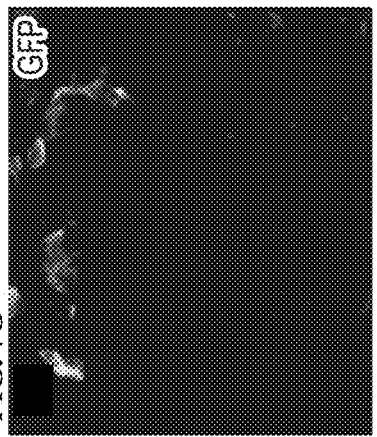

As vessel formation is governed by a complex molecular regulatory network, we aimed to determine a signaling basis for how stromal-progenitor cell interactions may guide the formation of vessels from P1 CD45− Tie2+ CD105+ PDGFRα− CD31+ and P2 CD45− Tie2+ CD105$^{high}$ PDGFRα+ CD31− donor cell populations. Microarray analysis demonstrated the P1 CD45− Tie2+ CD105+ PDGFRα− CD31+ stromal cell population was characterized by upregulation in PDGF ligand expression, whereas the P2 CD45− Tie2+ CD105 P2 CD45− Tie2+ CD105$^{high}$ PDGFRα+ CD31− progenitor subfraction expressed the PDGF receptor at high levels (FIG. 6). These data demonstrate a critical role for PDGF in regulation of vessel development, where PDGF acts as a stromal cue from the P1 CD45− Tie2+ CD105+ PDGFRα− CD31+ subfraction to guide P2 CD45− Tie2+ CD105$^{high}$ PDGFRα+ CD31− progenitor cells to form vessels.

To test the importance of PDGF signaling in vessel formation from the P1 CD45− Tie2+CD105+ PDGFRα− CD31+ and P2 CD45− Tie2+ CD105$^{high}$ PDGFRα+ CD31− cell populations, we cotransplanted both cell populations from actin-GFP mice with a saturating dose of a PDGFR antagonist. Explant of grafts under these conditions indicated complete ablation of vessel formation as GFP cells retained were characterized by a nondescript appearance and did not stain positive for markers of endothelial, smooth muscle, and pericyte origin (FIG. 7). Taken together, these findings confirm that PDGF is a key mediator of vessel formation from P1 CD45− Tie2+ CD105+ PDGFRα− CD31+ and P2 CD45− Tie2+ CD105$^{high}$ PDGFRα+ CD31− populations.

We next aimed to determine whether a combination of P1 CD45− Tie2+ CD105+ PDGFRα− CD31+ and P2 CD45− Tie2+ CD105$^{high}$ PDGFRα+ 31− SVF cells derived from adipose tissue of L2G mice could restore functional deficits in a model of murine hindlimb ischemia.

Preparations of Matrigel with 5×10$^5$ L2G P1 CD45− Tie2+ CD105+ PDGFRα− CD31+ and 5×10$^5$ P2 CD45− Tie2+ CD105$^{high}$ PDGFRα+ CD31− cells were delivered into the right hindlimb of immunodeficient Rag2/gamma(c) knockout mice following unilateral ligation of the common femoral artery. To assess the physiological consequences of the implanted cells, limb perfusion was monitored by laser Doppler imaging and quantified by calculating the signal ratio between the right ischemic limb and contralateral control limb (FIG. 2A). Mice injected with Matrigel only were observed to have low levels of revascularization due to spontaneous recovery. In sharp contrast, injection of P1 and P2 progenitor cells resulted in marked improvement of perfusion, with statistical significance emerging on day 7 post transplantation compared to the other groups (FIG. 2B). Characterization of donor cell grafts revealed functional recovery was mediated by de novo formation of functional GFP vessels, which anastomosed with host vasculature and revascularized the site of injury as demonstrated by presence of flowing blood in GFP positive vessels (FIG. 2C).

Previous studies have demonstrated endothelial progenitor cells hold great potential for cardiac regeneration, but suffer from poor survival in the ischemic heart and do not form functional vessels. Due to the marked improvements observed in the hindlimb ischemia model, we assessed whether the combinatorial delivery of P1 CD45− Tie2+ CD105+ PDGFRα− CD31+ and P2 CD45− Tie2+ CD105$^{high}$ PDGFRα+ CD31− cells from adipose SVF cells could restore function in a mouse model of myocardial infarction. We therefore derived P1 CD45− Tie2+ CD105+ PDGFRα− CD31+ and P2 CD45− Tie2+ CD105$^{high}$ PDGFRα+ CD31− cells from SVF of inguinal fat pads of L2G mice and transplanted 1×10$^6$ these cells into the myocardial border zone of immunodeficient mice undergoing ligation of the left anterior descending (LAD) artery (14). Cell survival was monitored longitudinally by BLI. Luciferase signal from P1 CD45− Tie2+ CD105+ PDGFRα− CD31+ and P2 CD45− Tie2+ CD105$^{high}$ PDGFRα+ CD31− cells persisted at robust levels for 8 weeks following delivery (FIG. 2D).

Cell engraftment in the border zone of the infarcted myocardium was confirmed by fluorescent dissecting microscope examination of explanted hearts from a subset of animals at day 60 post cell injection. Formation of de novo functional GFP vessels was detected in animals receiving the combination of P1 CD45− Tie2+ CD105+ PDGFRα− CD31+ and P2 CD45− Tie2+ CD105$^{high}$ PDGFRα+ CD31− cells. Importantly, donor GFP vessels in these animals were easily perfused by the DyLight-594 lectin dye indicating anastomosis with host vasculature. Many of the vessel structures were found to be carrying blood to the site of infarct as well (FIG. 2E). GFP vessels stained positive for markers of endothelial, smooth muscle, and pericyte lineage including CD31, smooth muscle actin (SMA), and NG2 (FIG. 2F).

Functional improvement was assessed in all treatment groups by small animal echocardiogram performed at baseline, day 2, day 14, day 28, and day 56 post-surgery. At day 2 post infarction, there was a significant decrease in the fractional shortening (FS) in all animals compared with that seen in baseline, consistent with successful induction of myocardial infarction (MI). At week 2, no significant change was found in any group (FIG. 2G-H). At weeks 4, 6, and 8, there was a trend toward improvement in FS for all three groups, but the change in the group receiving P1 CD45− Tie2+ CD105+ PDGFRα− CD31+ and P2 CD45− Tie2+ CD105$^{high}$ PDGFRα+ CD31− cells was found to be by far the most statistically significant.

Figure 8A:
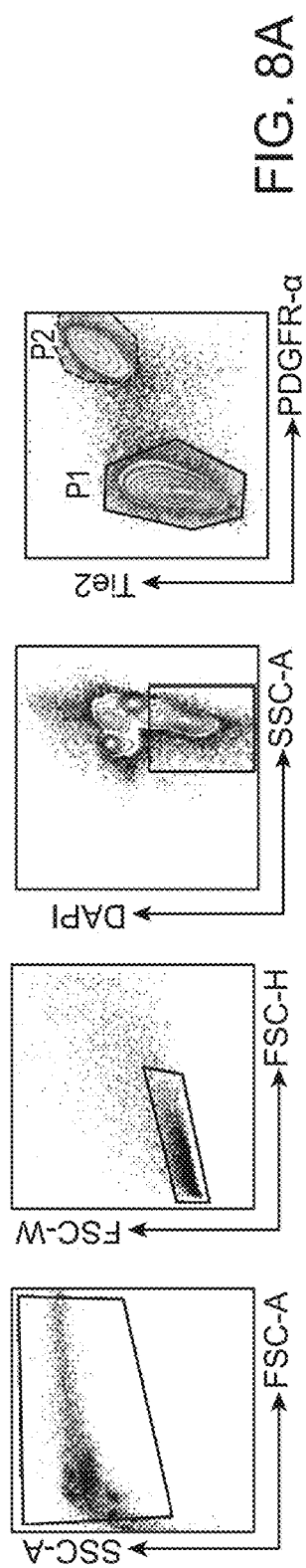
FIG. 8A-8C(iii). Isolation and transplantation of human vessel stem cell populations into a model of murine hindlimb ischemia.
Figure 8B:
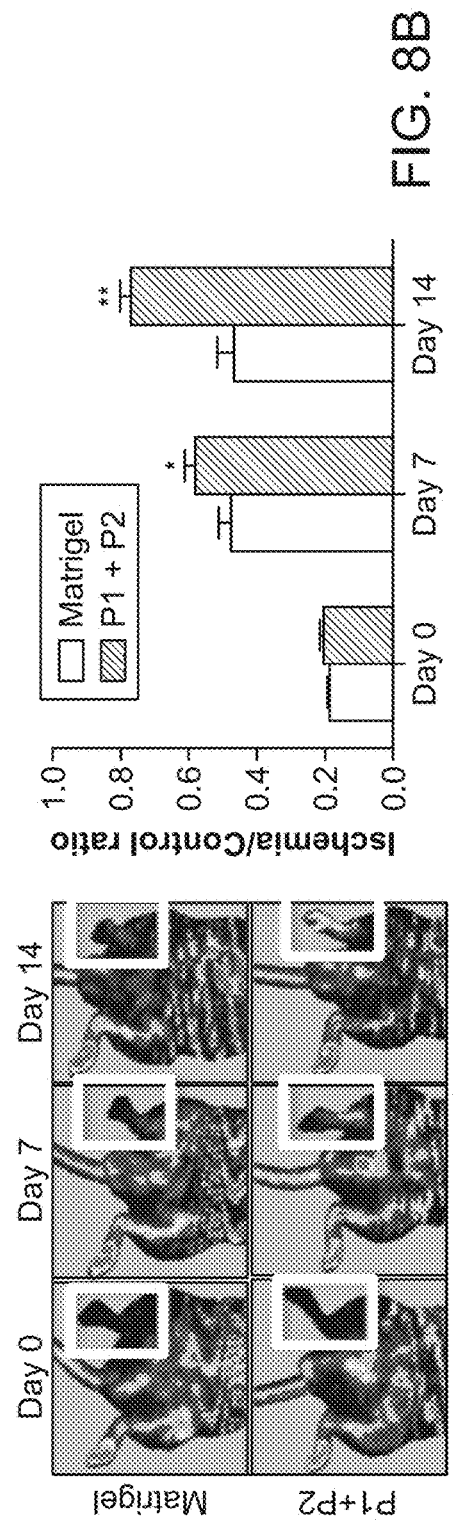
Figure 8C:
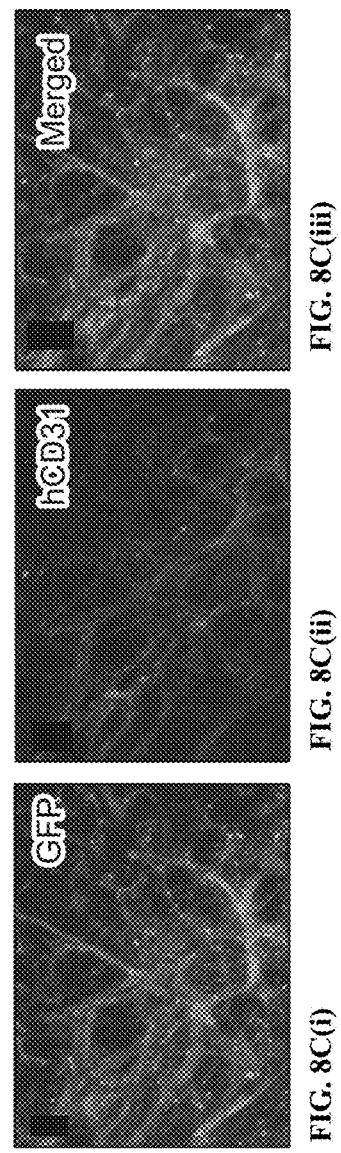

The successful in vivo generation of vessels from mouse stromal tissue to treat models of hindlimb ischemia and myocardial infarction prompted us to determine whether corresponding populations of P1 CD45− Tie2+ CD105+ PDGFRα− CD31+ and P2 CD45− Tie2+ CD105$^{high}$ PDGFRα+ CD31− cells exist in human stromal tissues. We therefore assessed the stromal SVF component of human abdominal lipoaspirate, which corresponds to the inguinal fat pads isolated from mice in which we originally discovered presence of these cell populations. FACs analysis of human lipoaspirate was found to contain both P1 CD45− Tie2+ PDGFRα−CD31+ and P2 CD45− Tie2+ PDGFRα+ CD31− populations, albeit at lower levels than the mouse (FIG. 8A). To determine whether these populations were capable of giving rise to vessels in vivo and ameliorating ischemic injury, we co-delivered the P1 and P2 populations into a xenotransplant model of hindlimb ischemia using immunodeficient SCID mice. Laser Doppler revealed significantly enhanced revascularization in animals receiving combination of human P1 CD45− Tie2+ PDGFRα− CD31+ and P2 CD45− Tie2+ PDGFRα+ CD31− cells as compared to controls that received vehicle alone (FIG. 8B). Infection of transplanted P1 and P2 cells with a GFP reporter virus prior to delivery followed by co-staining of explanted grafts for human CD31 revealed donor human cells formed endothelial cells within the transplants (FIG. 8C).

As shown in FIG. 9, vessel forming clones are amplified in response to ischemia in an animal model. The data demonstrate that there are vessel forming progenitors that can respond and amplify in response to ischemic stress. However the normal frequency of these progenitors may not be sufficient for full ischemic rescue, establishing a rationale for transplantation of progenitors to amplify new vessel formation.

In summary, we have utilized prospective FACs isolation to identify a novel P2 CD45− Tie2+ CD105$^{high}$ PDGFRα+ CD31− multipotent stromal progenitor subfraction that can differentiate into adipose and vascular cell fates. Our findings indicate these cells are endogenous to multiple organs with stromal components including bone marrow, lung tissue, and adipose tissue. We also demonstrate differentiation of P2 CD45− Tie2+ CD105$^{high}$ PDGFRα+ CD31− cells into vascular lineages is governed in part by signaling factors such as PDGF, which is secreted by P1 CD45− Tie2+ CD105+ PDGFRα− CD31+ stromal subfractions also inherent to the mesenchyme. In this brief communication, we have utilized the combination of P2 CD45− Tie2+ CD105$^{high}$ PDGFRα+ CD31− and P1 CD45− Tie2+ CD105+ PDGFRα− CD31+ cells for de novo formation of functional blood vessels in small animal models of hindlimb ischemia and myocardial infarction. While several recent publications have demonstrated the potential of mesenchymal tissue digests to integrate with existing or give rise to new blood vessels, these reports have not been able to identify specific vascular stem cell populations responsible for vessel formation. Differentiation of pluripotent stem cell populations into vessel lineages in vitro on biomaterials followed by surgical transplantation is another strategy for cell-based vascular therapy. However, the use of pluripotent stem cells is associated with significant risks such as immunogenicity and tumorigenicity as demonstrated by the recent hold on the first induced pluripotent stem cell clinical trial after only one patient was treated.

Enrichment of lineage committed vascular progenitor populations from adipose tissue followed by direct transplantation is a significant advance over current cell-based methods for treatment of ischemic injury because it has can be applied autologously without in vitro culture, and results in formation of de novo blood vessels. This strategy provides for autogenous "bedside tissue engineering" and can be used in the operating room for vascular surgery cases.

Methods

Animal Care. C57BL/Ka strain mice, including immunodeficient RAG2$^{−/−}$g/$^{−/−}$ $^d$ double knockout, actin-GFP, actin-RFP, and actin-Firefly Luciferase(Fluc)-GFP (L2G) strains were derived and maintained in our laboratory. All animals were housed in accordance with Stanford Animal Care and Use Committee and National Institutes of Health guidelines.

Statistical analysis. Normality distribution was studied with the Kolmogorov-Smirnov test (p<0.05). Statistically significant differences were determined using the Student's t-test or paired Student's t-test, with a set to 0.05 for genes with a normal distribution. Unless specified, data are expressed as average±SEM.

Isolation and transplantation of mouse adipose and vessel progenitors. Adult adipose and lung tissues were dissected, finely minced with razor blade and digested in collagenase (2.2 mg/mL) with DNase at 37° C. for 40 minutes under constant agitation. Total dissociated cells were filtered through 40 mm nylon mesh, pelleted at 200×g at 4° C., resuspended in staining media (2% fetal calf serum in PBS), blocked with rat IgG and stained with fluorochrome-conjugated antibodies against mouse CD45, Tie2, CD105, PDGFRα and CD31 for FACS on BD Aria II Flow Cytometer. Sorted adipose and vessel progenitors were pelleted by centrifugation, resuspended in 2 ml of matrigel, then injected underneath fat pads of neonatal and 8-12 weeks old anesthetized mice.

Isolation and transplantation of human vessel progenitors from adipose tissue. Human adipose lipoaspirates were obtained after informed consent from female patients (age 26-54). Fresh lipoaspirates were separated from blood and lipoaspiration fluids by passing through 100 um nylon mesh. Solid matter were then resuspended in collagenase digest buffer with Dnase [1 mg/ml Collagenase (Sigma) with 100 U/ml Dnase (Worthington) in M199 Media (Sigma)] then shaken in CERTOMAT® BS-1 Incubation-Shaking Cabinet at 37° C. for 40 minutes then sedimented on Histopaque 1119 Density gradient to remove blood and dead cells, washed, and pelleted at 200×g at 4° C. Cells were then plated on Lonza Endothelial Growth Media, and transduced with CMV-GFP expressing lenti-virus. 24 hours after transduction, Cells were lifted with collagenase, resuspended in staining media (2% fetal calf serum in PBS), blocked with rat IgG and stained with fluorochrome-conjugated antibodies against human CD45, Tie2, CD105, PDGFRα and CD31 for FACS on BD Aria II Flow Cytometer.

Histological analysis of blood vessel perfusion with lectin. Recipient mice were briefly anesthetized with Isoflurane, and then injected intravenously with 100 ul of DyLight 594 labeled Tomato Lectin (Vector Labs). 10 minutes after injection, mice were fully anesthetized with tribromoethanol (125-250 mg/kg body weight). Mice were then sacrificed and perfused with 10 mM EDTA in PBS to remove peripheral blood by accessing the left ventricle through an incision in the thoracic cavity. Incisions were also made to access engrafted areas that were then imaged with a Leica DMI6000B inverted microscope system.

Lentivirus production and transduction of human fat cells. HEK 293T cells (System Biosciences, Mountain View, Calif.) were plated at 50% confluency on 10 cm dishes and transfected with 12 μg of a construct expressing actin-GFP, 8 μg of packaging pPAX2, and 4 μg of VSVG plasmids using Lipofectamine 2000 (Invitrogen) as per the manufacturer's instructions. Supernatant was collected 24 and 48 h after transfection, filtered through a 0.45-μm pore-size cellulose acetate filter (Millipore, Billerica, Mass.), and mixed with PEG-it Virus Concentration Solution (System Biosciences) overnight at 4° C. Viruses were precipitated at 1,500 g at 4° C. on the next day and resuspended in PBS. Digested human lipoaspirate cells were infected with virus overnight for 24 h following sorting for P1 and P2 markers and prior to xeno-transplantation into immunodeficient Rag2/gamma(c) knockout animals.

Oil Red staining. Oil Red O (Sigma) was dissolved in 85% Propylene glycol to 0.5%. This stock Oil Red solution was then diluted further in PBS to 10% and added drop wise to fixed tissue specimens while imaging with Leica DMI6000B inverted microscope system.

Immunofluorescence microscopy. Immunofluorescence on cryopreserved specimens was performed using an M.O.M. immunodetection kit from Vector Laboratories according to manufacturer's instructions. Briefly, specimens were treated with a blocking reagent, and then probed with monoclonal antibody at 4° C. overnight. Specimens were next washed with PBS, probed with Alexa-dye conjugated antibodies, washed, coverslipped, and imaged with a Leica DMI6000B inverted microscope system.

Immunofluorescence on tissue cultured cell specimens were performed similar to cryopreserved specimens using an M.O.M. immunodetection kit from Vector Laboratories according to manufacturer's instructions. Briefly, cultured cells in 6 well to 96 well culture plates were washed with PBS and fixed in 2% PFA at 4° C. overnight. Specimens were treated with a blocking reagent, and then probed with monoclonal antibody at 4° C. overnight. Specimens were next washed with PBS, probed with Alexadye conjugated antibodies, washed, immersed in PBS, and imaged with a Leica DMI6000B inverted microscope system or with a Zeiss LSM710 confocal microscope. Monoclonal antibody to mouse and human CD31 pan-endothelial marker were purchased from eBiosciences, monoclonal antibody to smooth muscle actin was purchased from Abcam. Alexa-dye conjugated secondary antibodies were purchased from Molecular Probes.

Gene expression. Microarray analyses were performed on highly purified, double-sorted populations of P1 (CD45− Tie2+ CD105+ PDGFRα− CD31+) and P2 (CD45− Tie2+ CD105$^{high}$ PDGFRα+ CD31−). Each population was sorted in three independent sorts using cells isolated from 4 weeks-old mice. RNA was isolated with RNeasy Micro Kit (Qiagen, Germantown, Md.) as per manufacturer's instructions. RNA was twice amplified with a RiboAmp RNA amplification kit (Arcturus Engineering, Mountain View, Calif.). Amplified cRNA was streptavidin-labeled, fragmented, and hybridized to Affymetrix 430-2.0 arrays as recommended by the manufacturer (Affymetrix, Santa Clara). Arrays were scanned with a Gene Chip Scanner 3000 (Affymetrix) running GCOS 1.1.1. software. Raw microarray data were submitted to Gene Expression Commons, where data normalization was computed against the Common Reference, which is a large collection (n=11,939) of publically available microarray data from the National Center for Biotechnology Information Gene Expression Omnibus (NCBI GEO). Meta-analysis of the Common Reference also provides the dynamic range of each probe set on the array, and, in situations where there are multiple probe sets for the same gene, the probe set with the widest dynamic range was used for analysis. The Affymetrix Mouse Genome 430 2.0 Array includes 45,101 probesets, of which 17,872 annotated genes are measurable. Heat maps representing fold change of gene expression were generated in Gene Expression Commons.

Hindlimb ischemia model. Hindlimb ischemia was performed in Rag2 knockout immunodeficient animals as previously described. Mice were anesthetized with 1.5% isoflurane and the right hindlimb was opened to expose the femoral artery for ligation, after which $5\times10^5$ P1 and $5\times10^5$ P2 cells suspended in Matrigel were delivered into the gastrocnemius muscle using a 29 gauge Hamilton syringe (n=4 per group). Control animals received Matrigel alone. Skin was closed using 6-0 silk sutures. Revascularization was monitored by laser Doppler perfusion imaging. Animal studies were approved by the Administrative Panel on Laboratory Animal Care in Stanford University.

Measurement of blood flow by laser Doppler imaging. Following ligation of the right femoral artery, laser Doppler perfusion imaging was used to assess revascularization. Animals were knocked down using 1.5% isoflurane in oxygen, and hindlimb vascularization was monitored by laser Doppler perfusion imaging using a PeriScan PIM3 laser Doppler system (Perimed AB, Sweden) as previously described (n=4 per group) (24). Temperature was maintained at constant levels by keeping animals on heatpads set to 37° C. during measurement. Non-ligated contra-lateral hindlimbs served as controls. Perfusion was calculated as the ratio of the flow in the ischemic to control limbs.

Myocardial infarction and cell delivery. Rag2 knockout animals underwent induction of myocardial infarction by aseptic lateral thoracotomy and ligation of the left anterior descending (LAD) coronary artery, as previously described. Briefly, mice were anesthetized with inhaled 2% isoflurane, intubated, ventilated, and maintained under 1% inhaled isoflurane. Following a left thoracotomy and opening of the pericardium, the LAD artery was permanently ligated with a 9-0 Ethilon suture (Ethicon Inc., Somerville, N.J.). Infarction was visually confirmed by blanching of the anterior region of the left ventricle and dyskinesis. $5\times10^5$ P1 and $5\times10^5$ P2 cells ($1\times10^6$ cells total) or $1\times10^6$ unsorted adipose control cells were suspended in Matrigel and injected intramyocardially into the peri-infarct zone at 2 different sites for a total volume of 20 μL (n=6 per group). Control animals received a Matrigel injection if 20 μL (n=6). Following surgery and closure of the incision, all animals were placed in a temperature-controlled chamber until they resumed full alertness and mobility.

Bioluminescence imaging (BLI) to monitor in vivo survival of L2G transplanted cells. BLI was performed using the Xenogen IVIS 200 in vivo imaging system (Alameda, Calif.) as previously described. After intraperitoneal injections of reporter probe D-Luciferin (375 mg of luciferin/kg weight), animals were imaged with exposure times ranging from 2 seconds to 2 at days 2, 14, 28, and 56 post-surgery (n=6 per group). Imaging signals were quantified in units of maximum photons per second per square centimeter per steradian ($p/s/cm^2/sr$).

Left ventricular functional analysis with echocardiogram. Echocardiography was performed using a Siemens-Acuson Sequioa C512 system (Malvern, Pa.) equipped with a multi-frequency (8-14 MHz) 15L8 transducer on days 2, 14, 28, and 56 post-surgery (n=6 per group) as previously described. Briefly, animals were knocked down under 1.5% inhaled isoflurane and imaged in the supine position. The following formula was used to calculate fractional shortening (FS) from M-Mode short axis images of the left ventricle: FS= [Left ventricular end diastolic diameter (LVEDD)—Left end-systolic diameter (LVESD)]/[LVEDD].

What is claimed is:

1. A method for generating functional blood vessels in a human individual recipient, the method comprising:
    a) isolating P1 and P2 cells from human adipose stromal tissue, wherein P1 cells are defined as CD45$^-$ Tie2$^+$ CD105$^+$ PDGFRα$^-$ CD31$^+$ and P2 cells are defined as CD45$^-$ Tie2$^+$ CD105$^+$ PDGFRα$^+$ CD31$^-$; and
    b) administering to the human individual recipient a composition comprising an effective dose of the isolated P1 and P2 cells of step (a), at a site where regeneration of vessels is desired,
    wherein the isolated P1 and P2 cells are present in the composition at a ratio of 1:100 to 100:1, and
    wherein the isolated P1 and P2 cells are autologous with respect to the human individual recipient.

2. The method of claim 1, wherein the effective dose is from $10^3$ to $10^{10}$ total cells.

3. The method of claim 1, wherein the composition is provided in a matrix.

4. A method for generating functional blood vessels in a human individual recipient, the method comprising:
    a) isolating P1 and P2 cells from human adipose stromal tissue, wherein P1 cells are defined as CD45$^-$ Tie2$^+$ CD105$^+$ PDGFRα$^-$ CD31$^+$ and P2 cells are defined as CD45$^-$ Tier CD105$^+$ PDGFRα$^+$ CD31$^-$; and
    b) administering to the human individual recipient a composition comprising an effective dose of the isolated P1 and P2 cells of step (a), at a site where regeneration of vessels is desired,
    wherein the isolated P1 and P2 cells are present in the composition at a ratio of 1:100 to 100:1, and
    wherein the isolated P1 and P2 cells are allogeneic with respect to the human individual recipient.

5. The method of claim 1, wherein the P1 and P2 cells are freshly isolated from lipoaspirate.

6. The method of claim 1, wherein the P1 and P2 cells are isolated from adult human adipose stromal tissue.

7. The method of claim 1, wherein the human individual recipient suffers from ischemic cardiovascular disease.

8. The method of 7, wherein the human individual recipient suffers from coronary artery disease (CAD), peripheral arterial disease (PAD), or stroke.

9. A method for generating adipose tissue in a human individual recipient, the method comprising:
   a) isolating P2 cells from human adipose stromal tissue, wherein P2 cells are defined as $CD45^-$ $Tier$ $CD105^+$ $PDGFR\alpha^+$ $CD31^-$; and
   b) administering to the human individual recipient a composition comprising an effective dose of the isolated P2 cells of step (a), at a site where regeneration of adipose tissue is desired,
   wherein the isolated P2 cells are autologous with respect to the human individual recipient,
   wherein the composition lacks P1 cells, and
   wherein P1 cells are defined as $CD45^-$ $Tie2^+$ $CD105^+$ $PDGFR\alpha^{31}$ $CD31^+$.

* * * * *